(12) United States Patent
Azulay et al.

(10) Patent No.: US 11,774,532 B2
(45) Date of Patent: *Oct. 3, 2023

(54) RF SHIELDING CONDUIT IN AN MRI CLOSURE ASSEMBLY

(71) Applicant: Aspect Imaging Ltd., Shoham (IL)

(72) Inventors: Shmuel Azulay, Tel Aviv (IL); Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 13 days.

This patent is subject to a terminal disclaimer.

(21) Appl. No.: 16/545,764

(22) Filed: Aug. 20, 2019

(65) Prior Publication Data

US 2019/0369184 A1 Dec. 5, 2019

Related U.S. Application Data

(63) Continuation of application No. 15/452,916, filed on Mar. 8, 2017, now Pat. No. 10,386,432, which is a
(Continued)

(51) Int. Cl.
  *G01R 33/422* (2006.01)
  *G01R 33/48* (2006.01)
  (Continued)

(52) U.S. Cl.
  CPC .......... *G01R 33/422* (2013.01); *A61B 5/0046* (2013.01); *A61B 5/055* (2013.01);
  (Continued)

(58) Field of Classification Search
  CPC .............. G01R 33/422; G01R 33/0052; G01R 33/0076; G01R 33/48; A61B 5/0046; A61B 5/055; A61B 5/182
  See application file for complete search history.

(56) References Cited

U.S. PATENT DOCUMENTS

| 3,242,523 A | 3/1966 | Daley |
| 3,504,932 A | 4/1970 | Kozowyk |

(Continued)

FOREIGN PATENT DOCUMENTS

| CN | 101029922 | 9/2007 |
| CN | 201267472 | 7/2009 |

(Continued)

OTHER PUBLICATIONS

Hart, Segmented and Shielded Structures for Reduction of Thermal Expansion-Induced Tilt Errors, Precision Engineering Research Group Massachusetts Institute of Technology, Oct. 2004, pp. 443-458.

(Continued)

*Primary Examiner* — Rodney A Bonnette
(74) *Attorney, Agent, or Firm* — Loeb & Loeb LLP

(57) ABSTRACT

A radiofrequency (RF) shielding conduits that can be embedded within a doorframe and/or a door of a magnetic resonance imaging (MRI) room are disclosed. The RF shielding conduits can form, upon closing of door onto the doorframe, an RF shielding channel to enclose and/or allow passage of tubing of medical equipment extending from an interior of the MRI room to an environment that is external to the MRI room, while providing a RF shielding of the MRI room.

9 Claims, 11 Drawing Sheets

Related U.S. Application Data continuation-in-part of application No. 14/574,785, filed on Dec. 18, 2014, now Pat. No. 10,012,711.

(60) Provisional application No. 62/393,349, filed on Sep. 12, 2016, provisional application No. 61/917,362, filed on Dec. 18, 2013.

(51) Int. Cl.
  *A61B 5/00*    (2006.01)
  *A61B 5/055*   (2006.01)
  *G01R 33/00*   (2006.01)

(52) U.S. Cl.
  CPC ..... *G01R 33/0052* (2013.01); *G01R 33/0076* (2013.01); *G01R 33/48* (2013.01); *A61B 2562/182* (2013.01)

(56) References Cited

U.S. PATENT DOCUMENTS

| | | |
|---|---|---|
| 3,534,251 A | 10/1970 | Richards |
| 4,490,675 A | 12/1984 | Knuettel |
| 4,587,504 A | 5/1986 | Brown |
| 4,590,428 A | 5/1986 | Mueller |
| 4,646,046 A | 2/1987 | Vavrek |
| 4,910,461 A | 3/1990 | Van Vaals |
| 4,912,445 A | 3/1990 | Yamasaki |
| 4,977,585 A | 12/1990 | Boyd |
| 5,012,217 A | 4/1991 | Palkovich |
| 5,028,872 A | 7/1991 | Nakabayashi |
| 5,038,129 A | 8/1991 | Oue |
| 5,039,826 A | 8/1991 | Newland |
| 5,065,760 A | 11/1991 | Krause |
| 5,159,929 A | 11/1992 | Morris |
| 5,243,286 A | 9/1993 | Rzedzian |
| 5,304,932 A | 4/1994 | Carlson |
| 5,305,749 A | 4/1994 | Li |
| 5,323,776 A | 6/1994 | Blakeley |
| 5,572,131 A | 11/1996 | Rzedzian |
| 5,594,200 A | 1/1997 | Ramsey |
| 5,635,889 A | 6/1997 | Stelter |
| 5,659,281 A | 8/1997 | Pissanetzky |
| 5,986,531 A | 11/1999 | Carrozzi |
| RE36,679 E | 5/2000 | Zakhor |
| RE36,782 E | 7/2000 | Brown et al. |
| 6,188,015 B1 | 2/2001 | Curran, Sr. |
| 6,215,309 B1 | 4/2001 | Rzedzian |
| 6,346,814 B1 | 2/2002 | Carrozzi |
| 6,546,814 B1 | 4/2003 | Choe |
| 6,711,430 B1 | 3/2004 | Ferris |
| 6,801,038 B2 | 10/2004 | Carrozzi |
| 6,873,156 B2 | 3/2005 | Ferris |
| 6,995,562 B2 | 2/2006 | Laskaris |
| 7,071,692 B2 | 7/2006 | Branch |
| 7,141,974 B2 | 11/2006 | Edelstein |
| 7,157,911 B2 | 1/2007 | Suzuki |
| 7,171,256 B1 | 1/2007 | Graessle |
| 7,375,526 B2 | 5/2008 | Edelstein |
| 7,529,575 B2 | 5/2009 | Rezzonico |
| 7,633,294 B2 | 12/2009 | Leussler |
| 7,715,895 B1 | 5/2010 | Graessle |
| 7,772,503 B2 | 8/2010 | Ginanneschi |
| 7,801,613 B2 | 9/2010 | Li |
| 7,834,626 B2 | 11/2010 | Renz |
| 8,384,387 B1 | 2/2013 | Damadian |
| 8,807,084 B2 | 8/2014 | Rapoport |
| 8,851,018 B2 | 10/2014 | Rapoport |
| 8,896,310 B2 | 11/2014 | Rapoport |
| 9,301,724 B2 | 4/2016 | Mcknight |
| 9,470,769 B2 | 10/2016 | Bilu |
| 9,498,167 B2 | 11/2016 | Mostafavi |
| 9,562,956 B2 | 2/2017 | Rapoport |
| 9,597,246 B2 | 3/2017 | Rapoport |
| 9,655,291 B2 | 5/2017 | Ozaki |
| 9,974,705 B2 | 5/2018 | Rapoport |
| 10,012,711 B2* | 7/2018 | Rapoport ............ G01R 33/422 |
| 10,018,692 B2 | 7/2018 | Rapoport |
| 10,078,122 B2 | 9/2018 | Rapoport |
| 10,094,896 B2 | 10/2018 | Rapoport |
| 10,132,887 B2 | 11/2018 | Rapoport |
| 10,383,782 B2 | 8/2019 | Rapoport |
| 10,386,432 B2* | 8/2019 | Azulay ................ A61B 5/055 |
| 10,426,376 B2 | 10/2019 | Rapoport |
| 10,794,975 B2* | 10/2020 | Rapoport ............ G01R 33/422 |
| 2002/0057088 A1 | 5/2002 | Carrozzi |
| 2003/0016518 A1 | 1/2003 | Arz |
| 2003/0058502 A1 | 3/2003 | Griffiths |
| 2003/0088175 A1 | 5/2003 | Branch |
| 2005/0046422 A1 | 3/2005 | Edelstein et al. |
| 2005/0049491 A1 | 3/2005 | Rezzonico |
| 2006/0103383 A1 | 5/2006 | Tanabe |
| 2006/0186884 A1 | 8/2006 | Mallett |
| 2007/0026733 A1 | 2/2007 | Greim |
| 2007/0135704 A1 | 6/2007 | Branch |
| 2007/0232894 A1 | 10/2007 | Feenan |
| 2007/0276614 A1 | 11/2007 | Tan et al. |
| 2008/0060843 A1 | 3/2008 | Ginanneschi |
| 2008/0094062 A1 | 4/2008 | Edelstein |
| 2008/0186026 A1 | 8/2008 | Leussler |
| 2009/0072939 A1 | 3/2009 | Shen |
| 2009/0135578 A1 | 5/2009 | Mallett |
| 2009/0209846 A1 | 8/2009 | Bammer |
| 2010/0000780 A1 | 1/2010 | Zhu |
| 2011/0162652 A1 | 7/2011 | Rapoport |
| 2011/0304333 A1 | 12/2011 | Rapoport |
| 2012/0046722 A1 | 2/2012 | Olsen |
| 2012/0071745 A1 | 3/2012 | Rapoport |
| 2012/0073511 A1 | 3/2012 | Rapoport |
| 2012/0118630 A1 | 5/2012 | Jiang |
| 2012/0119742 A1 | 5/2012 | Rapoport |
| 2013/0109956 A1 | 5/2013 | Rapoport |
| 2013/0229181 A1 | 9/2013 | Biber |
| 2013/0328560 A1 | 12/2013 | Rapoport |
| 2014/0051976 A1 | 2/2014 | Rapoport |
| 2014/0099010 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0152302 A1 | 6/2014 | Rapoport |
| 2014/0152310 A1 | 6/2014 | Rapoport |
| 2014/0158062 A1 | 6/2014 | Rapoport |
| 2014/0230850 A1 | 8/2014 | Rapoport |
| 2014/0266203 A1 | 9/2014 | Rapoport |
| 2014/0300358 A1 | 10/2014 | Rapoport |
| 2014/0354279 A1 | 12/2014 | Dumoulin |
| 2014/0364722 A1 | 12/2014 | Dumoulin |
| 2014/0378821 A1 | 12/2014 | Rapoport |
| 2014/0378825 A1 | 12/2014 | Rapoport |
| 2015/0059655 A1 | 3/2015 | Rapoport |
| 2015/0065788 A1 | 3/2015 | Rapoport |
| 2015/0112186 A1 | 4/2015 | Rapoport |
| 2015/0137812 A1 | 5/2015 | Rapoport |
| 2015/0141799 A1 | 5/2015 | Rapoport |
| 2015/0168519 A1 | 6/2015 | Rapoport |
| 2015/0208994 A1 | 7/2015 | Rapoport |
| 2015/0212172 A1 | 7/2015 | Rapoport |
| 2015/0212173 A1 | 7/2015 | Rapoport |
| 2015/0253400 A1 | 9/2015 | Rapoport |
| 2015/0253401 A1 | 9/2015 | Rapoport |
| 2016/0131724 A1 | 5/2016 | Balaban |
| 2017/0146619 A1 | 5/2017 | Strauss |
| 2017/0176557 A1 | 6/2017 | Azulay |
| 2017/0256853 A1 | 9/2017 | Anderson |
| 2019/0216676 A1* | 7/2019 | Rapoport ............... A61B 5/055 |

FOREIGN PATENT DOCUMENTS

| | | |
|---|---|---|
| DE | 202012104183 | 2/2013 |
| DE | 202013105276 | 12/2013 |
| DE | 202013105276 U1 | 12/2013 |
| EP | 0825450 | 2/1998 |
| GB | 2436875 | 10/2007 |
| JP | S62207448 | 9/1987 |

(56) References Cited

FOREIGN PATENT DOCUMENTS

| | | |
|---|---|---|
| JP | H01303139 | 12/1989 |
| JP | 2005270422 | 10/2005 |
| WO | 1989004049 | 5/1989 |
| WO | 1993021645 | 10/1993 |
| WO | 2000001611 | 1/2000 |
| WO | 0016116 | 3/2000 |
| WO | 2002003090 | 1/2002 |
| WO | 2011008969 A1 | 1/2011 |
| WO | 2015071906 | 5/2015 |

OTHER PUBLICATIONS

Indian Examination Report for Application No. IN201647022689, dated Feb. 10, 2020, 6 pages.
International Preliminary report on patentability under Chapter II for PCT Application No. PCT/IL2014/51108 dated Feb. 2, 2016. 28 pages.
International Search Report for PCT Application No. PCT/IL2014/51108 dated Apr. 30, 2015. 3 pages.
Maramraju. Sri Harsha, et al. "Electromagnetic interactions in a shielded PET/MRI system for simultaneous PET/MR imaging in 9.4 T: Evaluation and results." IEEE Transactions on Nuclear Science 59.5 (2012): pp. 1892-1896.

* cited by examiner

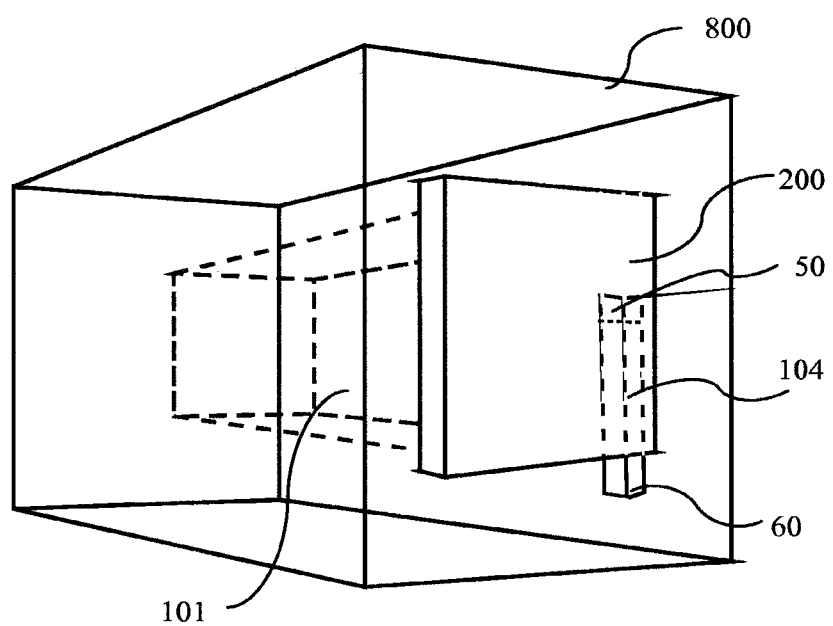
Fig. 1A
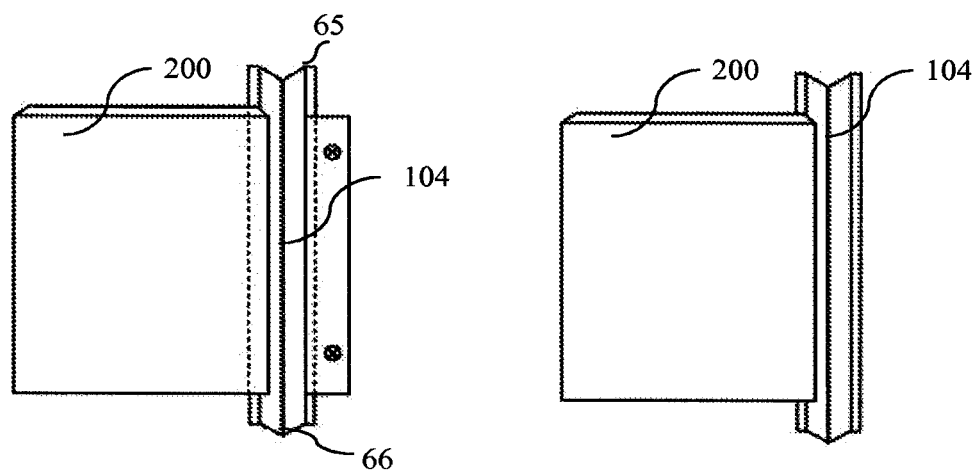
Fig. 1B
Fig. 1C

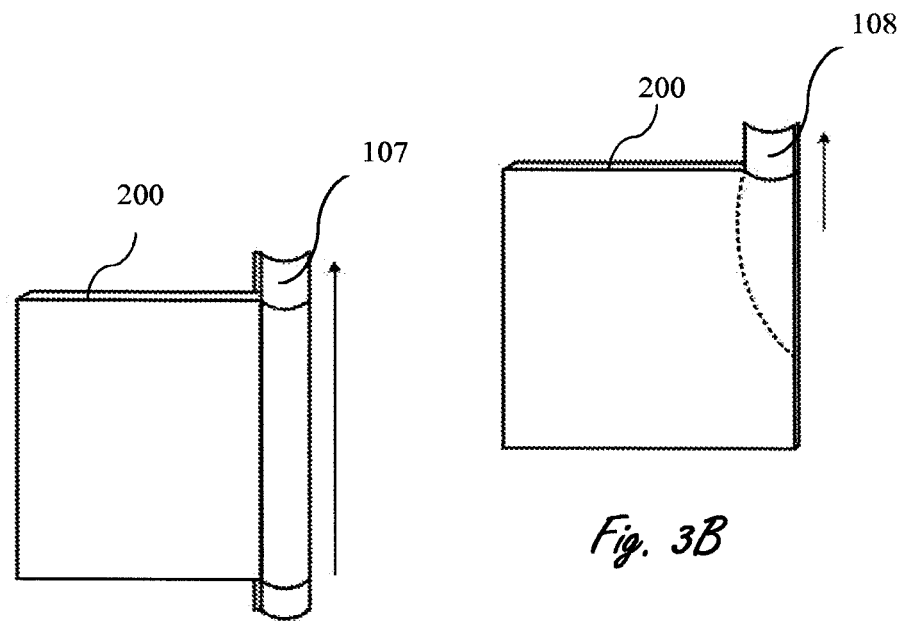
Fig. 3A
Fig. 3B
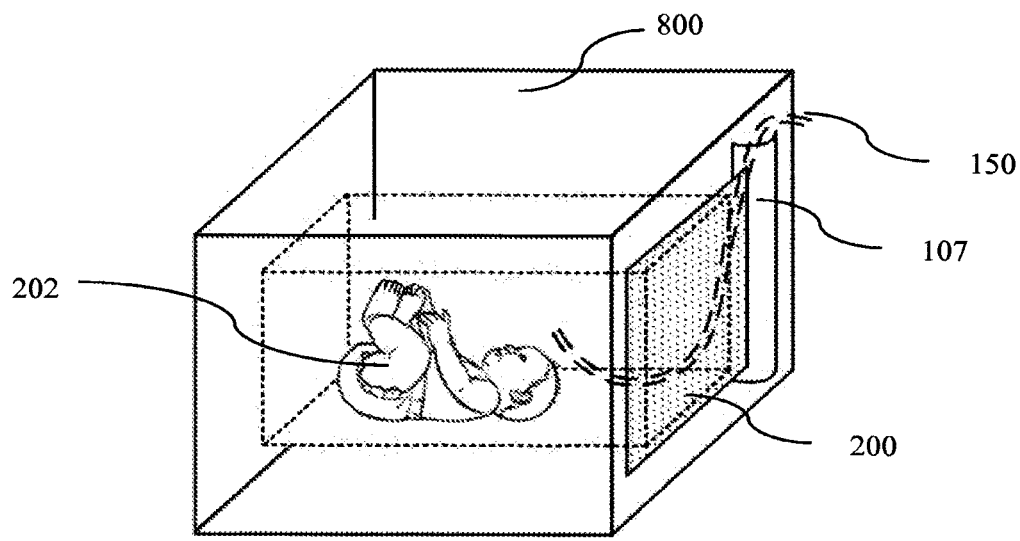
Fig. 3C

RF SHIELDING CONDUIT IN AN MRI CLOSURE ASSEMBLY

CROSS REFERENCE TO RELATED APPLICATIONS

This application is a continuation application of U.S. patent application Ser. No. 15/452,916, filed on Mar. 8, 2017, which claims the benefit of and priority to U.S. Provisional Application No. 62/393,349, filed on Sep. 12, 2016 and which is a continuation-in-part of U.S. patent application Ser. No. 14/574,785, filed on Dec. 18, 2014, which claims priority to U.S. Provisional Application No. 61/917,362, filed on Dec. 18, 2013, all of which are incorporated herein by reference in their entirety.

FIELD OF THE INVENTION

The present invention relates to the field of magnetic resonance imaging systems, and more particularly, to radiofrequency radiation shielding.

BACKGROUND OF THE INVENTION

MRI technology utilizes magnetism and radio frequency for imaging of patients for medical diagnosis and research. Electromagnetic interference (EMI) that is generated in the process of MRI negatively affects other devices in its vicinity such as medical electrical devices, computers, data transfer components, other scanning devices, etc. In addition EMI generated at an external source such as electric lines, television and radio signals, elevators, etc., can impede MRI operation and results.

Facilities providing MRI services build specially designed rooms that allow MRI procedures to be shielded from these interferences, while preventing leakage of the same interferences to the outside.

This shielding may include passive or active components to achieve magnetic and RF shielding. For example, to achieve RF shielding, the walls, floor and ceiling are built from sheets of conductive metal such as copper, aluminum, etc., including a door that maintains a closed circuit with the walls. Magnetic shielding could be provided by constructing a magnetic shield around the RF shield. A passive solution involves using magnetic shielding material, typically metal or metal alloy. These materials would need to be comprised of a very high permeability material such as "mu-metal". The second option would be an active magnetic cancellation system, that would typically include a magnetometer, controller, amplifier and compensation coils. This solution tends to be costly and requires adjusting and handling.

In order to provide a passage for systems such as air conditioning, electrical wiring, communication devices, medical equipment, etc., into EMI shielded rooms, means such as waveguide attenuators and RF filters are used. All fluid and air passing tubes are threaded through a conduit that is configured to attenuate EMI, and all electrical or conductive wiring is connected through an RF filter to avoid coupling of RF to the conductive wire. These means require pre-planning, and pre-insertion of each tube and cable to a previously constructed designated location.

Many patients are in need of medical support or monitoring during MRI. These include neonates, sedated patients, or other medically unstable patients. It is of critical importance to maintain life support and monitoring conditions of these patients also when undergoing MRI. Disconnecting medical equipment for the purpose of imaging a patient takes time and may cause patient stress, or induce medical complications.

An MRI scanner utilizes a very strong magnet, thus iron-containing unrestrained objects are drawn, making them airborne, into the magnet's bore. This hazardous phenomenon is known as the projectile, or missile, effect, which can potentially result in serious or fatal injuries to individuals in the scanner room. Even objects, as small as a stapler pin, may be a potential risk. Numerous severe accidents were recorded at MRI facilities because of pulled iron-containing objects. Keeping the MRI bore open for the passage of medical equipment may leave a space through which projectile objects could enter.

There is a long felt need for an apparatus that shields the passage of medical equipment from the inner space of the MRD bore to the external environment and contrariwise. This apparatus will provide physical, EMI, and RF shielding, while allowing passage for medical and life supporting equipment without compromising this shielding.

Magnetic resonance imaging (MRI) devices typically emit strong radiofrequency (RF) radiation which can cause disturbances and/or damage to surrounding electronic equipment. MRI devices can require dedicated MRI rooms and surroundings to prevent an external RF radiation from entering the MRI room and/or from a RF radiation emitted by the MRI device from exiting the MRI room. These issues can be particularly crucial when MRI devices are operated in proximity to a life supporting equipment that can be affected by the MRI device and/or can affect an operation of the MRI device.

Some patients undergoing an MRI imaging can require a continuous connection to, for example, the life supporting equipment, which can be positioned external to MRI room to prevent an interference with the MRI device as described above. Current solutions of passing a tubing of the life supporting equipment can include introducing a RF tunnels within a wall of the MRI room. Such RF tunnels typically require disconnecting the patient from the life supporting equipment to pass the tubing from the MRI room to an external environment, thereby endangering the patient.

SUMMARY OF THE INVENTION

The present invention provides, in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding conduit (RFSC), having apertures shaped to permit passage of medical equipment tubing from the external environment of the MRD to inner space of the bore, affixed to the closure assembly, wherein the conduit is characterized by a length (l) and width (w), l:w ratio is greater than a predefined value n, thereby providing RF shielding.

It is another object of the current invention to disclose the RFSC as defined in any of the above, wherein the RFSC is adapted by means of size and shape to permit passage of medical equipment tubing, from inner space of said MRD bore to the external environment.

It is another object of the current invention to disclose the RFSC as defined in any of the above, wherein the RFSC is connected in a non-protruding manner to the closure assembly, thereby indirect access is provided between the MRD bore and the external environment.

It is another object of the current invention to disclose the RFSC as defined in any of the above, wherein the RFSC is shaped to permit passage of the medical equipment tubing having a plurality of shapes and sizes.

It is another object of the current invention to disclose the RFSC as defined in any of the above, wherein the RFSC further comprises at least one designated placement for passing the medical equipment tubing.

It is another object of the current invention to disclose the RFSC as defined in any of the above, wherein the RFSC profile along the width is of a shape selected from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

It is another object of the current invention to disclose the RFSC as defined in any of the above, comprising an RFSC wall along the length, wherein the wall is of a shape selected from a group consisting of: straight, curved, polygonal, symmetrical, non-symmetrical and any combination thereof.

It is another object of the current invention to disclose the RFSC as defined in any of the above, wherein at least a portion of the RFSC aperture comprise a curved edge profile.

It is another object of the current invention to disclose the RFSC as defined in any of the above, wherein at least a portion of the RFSC is of a smoothed finish.

It is another object of the current invention to disclose the RFSC as defined in any of the above, wherein at least a portion of the RFSC is perforated, further wherein the perforations are of a length and diameter configured as a waveguide to attenuate RF selected from a group consisting of: 0 to about 1000 MHz, 0 to about 500 MHz, 0 to about 200 MHz and any combination thereof.

It is another object of the current invention to disclose the RFSC as defined in any of the above, wherein the RFSC is constructed as a detachable module.

It is another object of the current invention to disclose the RFSC as defined in any of the above, wherein at least a portion of the RFSC comprises electromagnetic conductive material.

It is another object of the current invention to disclose the RFSC as defined in any of the above, wherein the RFSC further comprises at least a portion of transparent material.

It is another object of the current invention to disclose the RFSC as defined in any of the above, comprising a longitudinal axis wall along the length, and at least two walls perpendicular to the longitudinal axis wall, wherein at least one of the walls is maneuverably connected to the longitudinal wall remaining in a fixed position.

It is another object of the current invention to disclose the RFSC as defined in any of the above, wherein the RFSC further comprises an RF detector system, further wherein the RF detection system comprises indicators selected from a group consisting of: audible, sensible, visual and any combination thereof.

It is another object of the current invention to disclose the RFSC as defined in any of the above, comprising at least one telescopic wall, wherein the wall allows change of the width, length, or depth as long as the ratio between the width and the length of the conduit remains greater than a predefined value n.

It is another object of the current invention to disclose the RFSC as defined in any of the above, wherein the RFSC is affixed to the closure assembly at a location of at least a portion of the perimeter between the closure assembly and the MRD.

It is another object of the current invention to disclose the RFSC as defined in any of the above, wherein the RFSC further comprises an open face along the length, thereby enabling removal of the medical equipment tubing without detaching it from any of the equipment ends.

It is another object of the current invention to disclose the RFSC as defined in any of the above, wherein the conduit is configured to attenuate the passage of frequencies selected from a group consisting of: 0 to about 1000 MHz, 0 to about 500 MHz, 0 to about 200 MHz and any combination thereof.

It is another object of the current invention to disclose the RFSC as defined in any of the above, wherein the conduit is configured to attenuate electromagnetic interference by means selected from a group consisting of: waveguide, RF filter, waveguide filter, attenuating material, and any combination thereof.

It is another object of the current invention to disclose the RFSC as defined in any of the above, wherein at least a portion of the RFSC comprises shielding selected from a group consisting of: magnetic shielding, RF shielding, physical shielding and any combination thereof.

It is another object of the current invention to disclose the RFSC as defined in any of the above, wherein at least a portion of the RFSC closes a conductive circuit with the closure assembly.

It is another object of the current invention to disclose the RFSC as defined in any of the above, wherein the RFSC is affixed to the closure assembly further comprising a hinge having at least one first connecting member connected to the MRD and at least one second connecting member, connected to the closure assembly, further wherein at least one first connecting member is maneuverably coupled to at least one second connecting member.

It is another object of the current invention to disclose the RFSC as defined in any of the above, wherein the hinge further comprises an emergency release mechanism, thereby enabling detachment of at least one hinged connected member.

It is another object of the current invention to disclose the RFSC as defined in any of the above, wherein the hinge member connected to the MRD is connected at a location selected from a group consisting of: at least a portion of the MRD external wall, within at least a portion of the MRD bore, at least a portion of the MRD aperture perimeter and any combination thereof.

It is another object of the current invention to disclose the RFSC as defined in any of the above, wherein the hinge member connected to the MRD is connected at a location, in reference to the MRD aperture, selected from a group consisting of: above, below, right, left, perpendicular to the floor, not perpendicular to the floor and any combination thereof.

It is another object of the current invention to disclose the RFSC as defined in any of the above, wherein the hinge connecting members are connected in a manner selected from a group consisting of: directly, indirectly and any combination thereof.

It is another object of the current invention to disclose the RFSC as defined in any of the above, wherein at least one hinge connecting member is maneuverable by a mean selected from a group consisting of: manual, automatic, self, remote control and any combination thereof.

The present invention provides, in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding hinge (RFSH) comprising at least one first connecting member connected to the MRD or open bore thereof and at least one second connecting member, connected to the closure assembly; at least one first connecting member is maneuverably coupled to at least one second connecting member; comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

It is another object of the current invention to disclose the RFSH as defined in any of the above, wherein the RFSH member connected to the MRD is connected at a location selected from a group consisting of: at least a portion of the MRD external wall, within at least a portion of the MRD bore, at least a portion of the MRD aperture perimeter and any combination thereof.

It is another object of the current invention to disclose the RFSH as defined in any of the above, wherein the hinged first connecting member is connected at a location, in respect to the MRD aperture, selected from a group consisting of: left, right, below, above and any combination thereof.

It is another object of the current invention to disclose the RFSH as defined in any of the above, wherein the hinged first connecting member is connected to the MRD in a manner selected from a group consisting of: directly, indirectly and any combination thereof.

It is another object of the current invention to disclose the RFSH as defined in any of the above, wherein the at least one hinge connecting member is maneuverable by a mean selected from a group consisting of: manual, automatic, self, remote control and any combination thereof.

It is another object of the current invention to disclose the RFSH as defined in any of the above, wherein at least a portion of the RFSH comprises a material selected from a group consisting of: diamagnetic, paramagnetic, ferromagnetic materials and combination thereof.

It is another object of the current invention to disclose the RFSH as defined in any of the above, wherein the RFSH is adapted by means of size and shape to permit passage of the medical equipment tubing, from the inner space of the MRD bore to the external environment.

It is another object of the current invention to disclose the RFSH as defined in any of the above, wherein the RFSH is shaped to permit passage of the medical equipment tubing having a plurality of shapes and sizes.

It is another object of the current invention to disclose the RFSH as defined in any of the above, wherein the RFSH further comprising at least one designated placement for passing the medical equipment tubing.

It is another object of the current invention to disclose the RFSH as defined in any of the above, wherein at least a portion of the RFSH aperture comprise a curved edge profile.

It is another object of the current invention to disclose the RFSH as defined in any of the above, wherein at least a portion of the RFSH is of a smoothed finish.

It is another object of the current invention to disclose the RFSH as defined in any of the above, comprising an emergency release mechanism, wherein the mechanism enables detachment of at least one the hinged connected member.

It is another object of the current invention to disclose the RFSH as defined in any of the above, wherein at least a portion of the RFSH comprises shielding selected from a group consisting of: magnetic shielding, RF shielding, physical shielding and any combination thereof.

It is another object of the current invention to disclose the RFSH as defined in any of the above, wherein at least a portion of the RFSH comprises electromagnetic conductive material.

It is another object of the current invention to disclose the RFSH as defined in any of the above, wherein at least a portion of the RFSC comprises transparent material.

It is another object of the current invention to disclose the RFSH as defined in any of the above, wherein the conduit further comprising an RF detector system, further wherein the RF detection system comprises indicators selected from a group consisting of: audible, sensible, visual and any combination thereof.

It is another object of the current invention to disclose the RFSH as defined in any of the above, wherein the conduit is configured to attenuate the passage of frequencies selected from a group consisting of: 0 to about 1000 MHz, 0 to about 500 MHz, 0 to about 200 MHz and any combination thereof.

It is another object of the current invention to disclose the RFSH as defined in any of the above, wherein the conduit is configured to attenuate electromagnetic interference by means selected from a group of: waveguide, RF filter, waveguide filter, attenuating material, and any combination thereof.

It is another object of the current invention to disclose the RFSH as defined in any of the above, wherein at least a portion of the RFSH closes an electromagnetic conductive circuit with the closure assembly.

It is another object of the current invention to disclose a method for RF shielding an MRD from its external environment generated EMI, and RF shielding the external environment from the MRD generated EMI, comprising steps of: (a) obtaining an MRD comprising: (i) a main longitudinal axis with a distal and proximal ends; (ii) an open bore extended along the axis and terminated by an aperture located in the proximal end; and (iii) a closure assembly shaped to fit the aperture comprising at least one conduit having apertures shaped to permit passage of medical equipment tubing from the external environment of the MRD to inner space of the bore, affixed to the closure assembly; (b) installing the closure assembly comprising the conduit; (c) inserting patient into the MRD bore; (d) passing the medical equipment tubing through the conduit; (e) covering the MRD bore with the closure assembly; and (f) imaging patient, wherein the conduit is characterized by a length (l) and width (w), l:w ratio is greater than a predefined value n, thereby providing RF shielding.

It is another object of the current invention to disclose a method as described above, additionally comprising a step of connecting the conduit in a non-protruding manner to the closure assembly, thereby indirect access is provided between the MRD bore and the external environment.

It is another object of the current invention to disclose a method as described above, additionally comprising a step of connecting at least one designated placement for passing the medical equipment tubing within the conduit.

It is another object of the current invention to disclose a method as described above, additionally comprising a step of connecting the RFSC constructed as a detachable module.

It is another object of the current invention to disclose a method as described above, additionally comprising a step of connecting an RF detector system, further selecting the RF detection system indicators from a group consisting of: audible, sensible, visual and any combination thereof.

It is another object of the current invention to disclose a method as described above, additionally comprising a step of obtaining a conduit comprising at least one telescopic wall.

It is another object of the current invention to disclose a method as described above, additionally comprising a step of changing the wall width, length, or depth as long as the ratio between the width and the length of the conduit remains greater than a predefined value n.

It is another object of the current invention to disclose a method as described above, additionally comprising a step of obtaining the RFSC comprising an open face along the length, It is another object of the current invention to disclose a method as described above, additionally comprising a step of installing or removing the medical equipment tubing without detaching it from any of the equipment ends.

It is another object of the current invention to disclose a method as described above, wherein the RFSC is affixed to a closure assembly further comprising a hinge having at least one first connecting member connected to the MRD and at least one second connecting member, connected to the closure assembly, further wherein the at least one first connecting member is maneuverably coupled to the at least one second connecting member.

It is another object of the current invention to disclose a method as described above, additionally comprising a step of emergency releasing the patient by detaching of at least one the hinged connected member.

It is another object of the current invention to disclose a method as described above, additionally comprising a step of maneuvering at least one the hinge connecting member by a mean selected from a group consisting of: manual, automatic, self, remote control and any combination thereof.

It is another object of the current invention to disclose a method as described above, additionally comprising a step of obtaining an RF shielding hinge (RFSH) comprising at least one first connecting member connected to the MRD and at least one second connecting member, connected to the closure assembly; the at least one first connecting member is maneuverable coupled to the at least one second connecting member, comprising a conduit, having apertures shaped to permit passage of medical equipment tubing from the external environment of the MRD to inner space of the bore;

It is another object of the current invention to disclose a method as described above, additionally comprising a step of maneuvering at least one the hinge connecting member by a mean selected from a group consisting of: manual, automatic, self, remote control and any combination thereof.

It is another object of the current invention to disclose a method as described above, additionally comprising a step of connecting at least one designated placement for passing the medical equipment tubing to the RFSH.

It is another object of the current invention to disclose a method as described above, additionally comprising a step of emergency releasing the patient by detaching of at least one the hinged connected member.

It is another object of the current invention to disclose a method as described above, additionally comprising a step of connecting an RF detector system, further selecting RF detection system indicators form a group consisting of: audible, sensible, visual and any combination thereof.

It is another object of the current invention to disclose a method for manufacturing an RF shielding conduit (RFSC) in an MRD closure assembly comprising steps of: (a) obtaining a closure assembly shaped to fit an aperture of an MRD bore; (b) defining dimensions of the RFSC a length (l) and width (w), so that l:w ratio is greater than a predefined value n\ (c) defining dimensions of the RFSC to permit passage of medical equipment tubing within; (d) defining the location of the RFSC within the closure assembly to enable access to the handler; (e) forming defined the RFSC; and (f) connecting the RFSC to the closure assembly, wherein, the closure assembly comprises a conduit having a longitudinal axis, comprising a proximal end having a cutout facing the MRD bore, and a distal end having a cutout facing environment external of the MRD.

It is another object of the current invention to disclose a method as described above, additionally comprising a step of adapting the RFSC is by means of size and shape to permit passage of the medical equipment tubing, from inner space of the MRD bore to the external environment.

It is another object of the current invention to disclose a method as described above, additionally comprising a step of connecting the RFSC in a non-protruding manner to the closure assembly, thereby providing indirect access between the MRD bore and the external environment.

It is another object of the current invention to disclose a method as described above, additionally comprising a step of shaping the RFSC to permit passage of the medical equipment tubing having a plurality of shapes and sizes.

It is another object of the current invention to disclose a method as described above, additionally comprising a step of designing at least one designated placement for passing the medical equipment tubing within the RFSC.

It is another object of the current invention to disclose a method as described above, additionally comprising a step of selecting RFSC profile along the width is from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

It is another object of the current invention to disclose a method as described above, additionally comprising a step of selecting an RFSC wall shape along the longitudinal axis, from a group consisting of: straight, curved, polygonal, symmetrical, non-symmetrical and any combination thereof.

It is another object of the current invention to disclose a method as described above, additionally comprising a step of forming at least a portion of the RFSC aperture comprising a curved edge profile.

It is another object of the current invention to disclose a method as described above, additionally comprising a step of forming at least a portion of the RFSC in a smoothed finish.

It is another object of the current invention to disclose a method as described above, additionally comprising a step of perforating the RFSC, further the perforations are of a length and diameter configured as a waveguide to attenuate RF selected from a group consisting of: 0 to about 1000 MHz, 0 to about 500 MHz, 0 to about 200 MHz and any combination thereof.

It is another object of the current invention to disclose a method as described above, additionally comprising a step of constructing the RFSC as a detachable module. It is another object of the current invention to disclose a method as described above, additionally comprising a step of making at least a portion of the RFSC comprising electromagnetic conductive material.

It is another object of the current invention to disclose a method as described above, additionally comprising a step of making at least a portion of the RFSC comprising transparent material.

It is another object of the current invention to disclose a method as described above, additionally comprising a step of defining the RFSC comprising a longitudinal axis wall, and at least two walls perpendicular to the longitudinal axis wall, further at least one of the walls is maneuverably connected to the longitudinal wall remaining in a fixed position.

It is another object of the current invention to disclose a method as described above, additionally comprising a step of connecting an RF detector system, further selecting the RF detection system indicators from a group consisting of: audible, sensible, visual and any combination thereof.

It is another object of the current invention to disclose a method as described above, additionally comprising a step of defining at least one conduit telescopic wall, allowing change of the width, length, or depth as long as the ratio between the width and the length of the conduit remains greater than a predefined value n.

It is another object of the current invention to disclose a method as described above, additionally comprising a step of affixing the RFSC to the closure assembly at a location of at least a portion of the perimeter between the closure assembly and the MRD.

It is another object of the current invention to disclose a method as described above, additionally comprising a step of defining the RFSC further comprising an open face along the length, thereby enabling removal of the medical equipment tubing without detaching it from any of the equipment ends.

It is another object of the current invention to disclose a method as described above, additionally comprising a step of configuring the conduit to attenuate the passage of frequencies selected from a group consisting of: 0 to about 1000 MHz, 0 to about 500 MHz, 0 to about 200 MHz and any combination thereof.

It is another object of the current invention to disclose a method as described above, additionally comprising a step of configuring the conduit to attenuate electromagnetic interference by means selected from a group of: waveguide, RF filter, waveguide filter, attenuating material, and any combination thereof.

It is another object of the current invention to disclose a method as described above, additionally comprising a step of making at least a portion of the RFSC comprising shielding selected from a group consisting of: magnetic shielding, RF shielding, physical shielding and any combination thereof.

It is another object of the current invention to disclose a method as described above, additionally comprising a step of forming at least a portion of the RFSC in a shape closing a conductive circuit with the closure assembly.

It is another object of the current invention to disclose a method as described above, additionally comprising a step of affixing the RFSC to a closure assembly further comprising a hinge having at least one first connecting member connected to the MRD and at least one second connecting member, connected to the closure assembly, further wherein the at least one first connecting member is maneuverably coupled to the at least one second connecting member.

It is another object of the current invention to disclose a method as described above, additionally comprising a step of including an emergency release mechanism to the hinge, thereby enabling detachment of at least one the hinged connected member.

It is another object of the current invention to disclose a method as described above, additionally comprising a step of selecting the location of the connection between the hinge member to the MRD from a group consisting of: at least a portion of the MRD external wall, within at least a portion of MRD bore, at least a portion of the MRD aperture perimeter and any combination thereof.

It is another object of the current invention to disclose a method as described above, additionally comprising a step of selecting the location, in reference to the MRD aperture, of the connection between the hinge member to the MRD from a group consisting of: above, below, right, left, perpendicular to the floor, not perpendicular to the floor and any combination thereof.

It is another object of the current invention to disclose a method as described above, additionally comprising a step of connecting the hinge connecting members in a manner selected from a group consisting of: directly, indirectly and any combination thereof.

It is another object of the current invention to disclose a method as described above, additionally comprising a step of selecting a mean of maneuvering at least one the hinge connecting member from a group consisting of: manual, automatic, self, remote control and any combination thereof.

It is another object of the current invention to disclose a method as described above, additionally comprising a step of defining the conduit in at least a portion of an RF shielding hinge (RFSH), having at least one first connecting member connected to the MRD and at least one second connecting member, connected to the closure assembly; the at least one first connecting member is maneuverable coupled to the at least one second connecting member.

It is another object of the current invention to disclose a method as described above, additionally comprising a step of connecting the RFSH member to the MRD at a location selected from a group consisting of: at least a portion of the MRD external wall, within at least a portion of MRD bore, at least a portion of the MRD aperture perimeter and any combination thereof.

It is another object of the current invention to disclose a method as described above, additionally comprising a step of connecting the hinged first connecting member to the MRD at a location, in respect to the MRD aperture, selected from a group consisting of: left, right, below, above and any combination thereof.

It is another object of the current invention to disclose a method as described above, additionally comprising a step of connecting the hinged first connecting member to the MRD in a manner selected from a group consisting of: directly, indirectly and any combination thereof.

It is another object of the current invention to disclose a method as described above, additionally comprising a step of selecting a mean of maneuvering at least one the hinge connecting member from a group consisting of: manual, automatic, self, remote control and any combination thereof.

It is another object of the current invention to disclose a method as described above, additionally comprising a step of forming at least a portion of the RFSH comprising a material selected from a group consisting of: diamagnetic, paramagnetic, ferromagnetic materials and combination thereof.

It is another object of the current invention to disclose a method as described above, additionally comprising a step of adapting the RFSH by means of size and shape to permit passage of the medical equipment tubing, from the inner space of the MRD bore to the external environment.

It is another object of the current invention to disclose a method as described above, additionally comprising a step of shaping the RFSH to permit passage of the medical equipment tubing having a plurality of shapes and sizes.

It is another object of the current invention to disclose a method as described above, additionally comprising a step of designing at least one designated placement for passing the medical equipment tubing within the conduit.

It is another object of the current invention to disclose a method as described above, additionally comprising a step of forming at least a portion of the RFSH aperture comprising a curved edge profile.

It is another object of the current invention to disclose a method as described above, additionally comprising a step of forming at least a portion of the RFSH in a smoothed finish.

It is another object of the current invention to disclose a method as described above, additionally comprising a step of including an emergency release mechanism wherein the mechanism enables detachment of at least one the hinged connected member.

It is another object of the current invention to disclose a method as described above, additionally comprising a step of selecting shielding of at least a portion of the RFSH from a group consisting of: magnetic shielding, RF shielding, physical shielding and any combination thereof.

It is another object of the current invention to disclose a method as described above, additionally comprising a step of forming at least a portion of the RFSH comprising electromagnetic conductive material.

It is another object of the current invention to disclose a method as described above, additionally comprising a step of forming at least a portion of the RFSC comprising transparent material.

It is another object of the current invention to disclose a method as described above, additionally comprising a step of connecting an RF detector system, further selecting RF detection system indicators selected form a group consisting of: audible, sensible, visual and any combination thereof.

It is another object of the current invention to disclose a method as described above, additionally comprising a step of configuring the RFSH to attenuate the passage of frequencies selected from a group consisting of: 0 to about 1000 MHz, 0 to about 500 MHz, 0 to about 200 MHz and any combination thereof.

It is another object of the current invention to disclose a method as described above, additionally comprising a step of configuring to attenuate electro magnetic interference by means selected from a group of: waveguide, RF filter, waveguide filter, attenuating material, and any combination thereof.

It is another object of the current invention to disclose a method as described above, additionally comprising a step of forming at least a portion of the RFSC in a shape closing an electromagnetic conductive circuit with the closure assembly.

It is another object of the current invention to disclose a standard of care protocol for magnetic resonance imaging a patient placed within MRD bore, connected to medical equipment, whilst not leaking RF into the MRD characterized by providing in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding conduit (RFSC), having apertures shaped to permit passage of medical equipment tubing from the external environment of the MRD to inner space of the bore, affixed to the closure assembly, the conduit is characterized by a length (l) and width (w), l:w ratio is greater than a predefined value n, thereby providing RF shielding, wherein at least one of the following is held true: (a) the average number of MRD associated patient's health complications when utilizing the RFSC is n times lower than the average number of patient's MRI associated health complications, n is equal or greater than 1.05; (b) the average number of insurable claims of a selected from a group consisting of: manufacturer, handler, user, operator, medical care personal, medical facility, medical facility management or any combination thereof when utilizing the RFSC is m times lower than patient MRI associated insurable claims; m is equal or greater than 1.05; (c) the average number of repeated MRI due to EMI when utilizing the RFSC is p times lower than the average number of repeated MRI; p is equal or greater than 1.05; (d) the average number of misinterpreted MRI due to EMI produced artifacts when utilizing the RFSC is o times lower than the average number of repeated MRI; o is equal or greater than 1.05; (e) the average number of patients detached from medical equipment during MRI when utilizing the RFSC is z times lower than the average number patients detached from medical equipment during MRI; z is equal or greater than 1.05; and (f) the average number of patient's health complications due to EMI interfering with medical equipment is u times higher than when utilizing the RFSC assembly; u is equal or greater than 1.05.

One aspect of the present invention provides a radiofrequency (RF) shielding conduit to be embedded within at least one of: a doorframe, a door or any combination thereof of a magnetic resonance imaging (MRI) room, the RF shielding conduit including: a first and a second wall, the first wall and the second wall are substantially parallel to a longitudinal axis of the doorframe, each of the first wall and the second wall having an opening, wherein the opening of the first wall is at an opposite end with respect to the opening of the second wall; a third wall substantially parallel to the longitudinal axis of the doorframe, the third wall is connected to the first wall and the second wall; and a gap bounded by the first wall, the second wall and the third wall, wherein the RF shielding conduit forms upon closing of a door onto the doorframe a RF shielding channel to provide a RF shielding of the MRI room.

In some embodiments, providing of the RF shielding of the MRI room includes preventing an external RF radiation from entering an interior of the MRI room and from a radiation emitted by a MRI device from exiting the interior of the MRI room.

In some embodiments, the first, second and third walls include a conductive material.

In some embodiments, the first wall is closer to an interior of the MRI room and the second wall is closer to an environment that is external to the MRI room.

In some embodiments, the gap having a substantially U-shape in a transverse direction with respect to the longitudinal axis.

In some embodiments, the gap receives tubing of medical equipment extending from an interior of the MRI room to an environment that is external to the MRI room.

In some embodiments, the RF shielding channel encloses the tubing of medical equipment extending from the interior of the MRI room to the environment that is external to the MRI room.

In some embodiments, the RF shielding tunnel having a longitudinal dimension and a transverse dimension and wherein a ratio of the longitudinal dimension to transverse dimension is at least 5:1.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1A is a schematic illustration of an MRD connected to a closure assembly in a rectangular embodiment for shutting the entrance of an MRD bore presented in its open configuration;

FIG. 1B is a schematic illustration, in an outside view, of a closure assembly, in a rectangular embodiment inserted within a conduit of a multifaceted shape;

FIG. 1C is a schematic illustration, in an inside view, of a closure assembly, in a rectangular embodiment inserted within a conduit of a multifaceted shape; the conduit is positioned at the left side of the closure assembly;

FIG. 3A is a schematic illustration, in a side view, of an embodiment of a RF shielding hinge with a conduit (107);

FIG. 3B is a schematic illustration, in a side view, of an embodiment of a RF shielding hinge with a conduit (108) along a portion of the hinge;

FIG. 3C is a schematic illustration presenting an embodiment of an MRD with a closure assembly harboring a RF shielding hinge in which tubing is passed through;

FIG. 4A is a schematic illustration presenting an embodiment of an RF shielding hinge (100), in which tubing is passed through;

DETAILED DESCRIPTION OF THE INVENTION

Figure 1D:
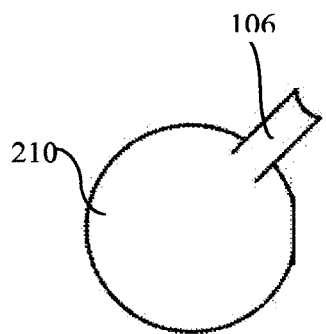
FIG. 1D is a schematic illustration, in an outside view, of a closure assembly in a circular embodiment and comprises a conduit of a cylindrical shape.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. The present invention provides a closure assembly for an MRI bore with means to facilitate the passage of medical equipment.

The essence of the present invention is to provide a RF shielding conduit, affixed to an MRD closure assembly that allows covering of an MRD bore aperture, thereby providing an RF shielded passage for medical equipment to within the MRD bore from the external environment and contrariwise. In addition, the present invention provides an RF shielding hinge comprising a conduit, in a closure assembly further providing an RF shielded passage for medical equipment to within the MRD bore from the external environment and contrariwise.

The RF shielding conduit of the present invention will increase the safety of MRI as the patient will be connected to medical equipment whilst not leaking EMI to and from the MRD. Further, the patient will be protected from ferromagnetic pulled objects while maintaining a passage to the inner space of an MRD bore for medical equipment.

Generally, radiofrequency (RF) shielding conduits that can be embedded within a doorframe and/or a door of a magnetic resonance imaging (MRI) room are provided. The RF shielding conduits can form, upon closing of the door onto the doorframe, an RF shielding channel to enclose and/or allow passage of tubing of medical equipment extending from an interior of the MRI room to an environment that is external to the MRI room, while providing a RF shielding of the MRI room.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. The term "closed bore MRI" refers herein after to MRI scanner that has a large cylinder-shape tube inside a MRI magnet.

The term "MRD bore" interchangeably refers hereinafter to a large cylinder-shaped tube of a MRI scanner which is designed to accommodate a patient.

The term "inner space of MRD bore" refers hereinafter to inner volume of a MRI bore.

The term "external environment" refers hereinafter to the external space outside of an MRI scanner.

The term "about" refers hereinafter to 20% more or less than the defied value.

The term "patient" interchangeably refers herein after to a term selected from a group of: neonate, baby, infant, toddler, child, adolescent, adult, elderly, etc.; further this term refers to person or animal.

The term "medical equipment" interchangeably refers hereinafter to all devices, tubes, connectors, wires, liquid carriers, needles, sensors, etc., that are used by medical staff in association with the patient. This medical equipment is used for various purposes such as life support, ventilating, temperature regulating, MRI contras solution injection, monitoring of cardio and breathing rates, viewing the patient, fluids transport, performing surgical operation, moving at least a part of the patient, etc.

The term "medical equipment tubing" interchangeably refers hereinafter to all tubes, cables, connectors, wires, liquid carriers, gas carriers, electrical wires, monitoring cables, viewing cables, data cables etc. that is used in connection to medical equipment or physical environment maintenance or monitoring.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non-transparent materials for means of strength and/or conductivity such as metallic wires.

The term "equipment ends" refers hereinafter to any equipment that has a longitudinal axis with a distal end and a proximal end. This could be medical life support or monitoring equipment comprising tubes that are connected at their distal end to a patient and on their proximal end to the apparatus body.

The term "electromagnetic interference" interchangeably refers hereinafter to electromagnetic interference (EMI), and radio-frequency interference (RFI), derived from electromagnetic radiation, electromagnetic induction, magnetism, electrostatic fields etc., that affect any electrical circuit, or imaging device such as MRD, NMR, ESR, NQR, CT, US, etc. This interference is derived from any source natural or artificial such as earth magnetic field, atmospheric noise, moving masses of metal, electrical lines, subways, cellular communication equipment, electrical devices, TV and radio stations, elevators, etc. This interference can interrupt, obstruct, degrade, limit, result in false data, etc., the effective performance of the circuit or device.

The term "electromagnetic shielding" refers hereinafter to a practice or device aimed at reducing the electromagnetic field in a space by blocking the field with barriers made of conductive or magnetic materials. The shielding can reduce the affect of radio waves, electromagnetic fields and electrostatic fields. Shielding is typically applied to isolate devices from the external environment, and to cables to isolate wires from the environment through which the cable runs.

The term "magnetic shielding" refers hereinafter to a practice or device aimed at reducing the magnetic field in a space. This is usually achieved by applying high permeability and low coersivity metal alloys that draw the magnetic shield and contain it such as nickel containing alloys.

The term "RF shielding" refers hereinafter to electromagnetic shielding that blocks radio frequency electromagnetic radiation.

The term "RF attenuation properties" interchangeably refers hereinafter to properties that do not allow passage though of defined RF waves. This could be achieved by means such as waveguides designed to attenuate RF, RF filters, waveguide filters, etc.

The term "value of n" interchangeably refers herein after to the numerical value relating to the ratio between the length (l) and the width (w) of the conduit; l:w ratio is greater than a predefined value n, further the numerical value of n is selected from a group consisting of: $2.5<n<6$, $4<n<6$, $4<n<9$ and any combination thereof.

The term "waveguide" interchangeably refers hereinafter to a structure that guides waves, such as electromagnetic waves or sound waves. The geometry of a waveguide reflects its function. Wave guides are constructed in different forms such as a hollow shape, solid rod, wire, etc. They are typically constructed from either conductive or dielectric materials. The frequency of the transmitted wave also dictates the shape of a waveguide. As depicted in Wikipedia, electromagnetic wave propagation along the axis of the waveguide is described by the wave equation, which is derived from Maxwell's equations, and where the wavelength depends upon the structure of the waveguide, and the material within it (air, plastic, vacuum, etc.), as well as on the frequency of the wave.

The term "waveguide cutoff interchangeably refers hereinafter to a boundary in a system's frequency response at which energy flowing through the system begins to be reduced, attenuated or reflected rather than passing through. This property is a derivate of the size and shape of the waveguide. Therefore waveguides are designed to attenuate a specific range of frequencies having a defined amplitude, and wave length that are not able physically to propagate within a specific geometry.

The term "cutoff frequency", (fc) interchangeably refers hereinafter to the frequency beyond which the waveguide no longer effectively contains EMI. Thus, any exciting frequency lower than the cutoff frequency will be attenuated, rather than propagated through the waveguide.

The term "RF filter" interchangeably refers hereinafter to components designed to filter signals in the MHz to GHz frequency ranges. This frequency range is the range used by most broadcast radio, television, wireless communication. These components exert some kind of filtering on the signals transmitted or received. The filters could be active or passive such as waffle-iron filter, mechanical RF filter, etc. RF filters are usually placed when there is need to pass an electrical wire in or out of an MRD enclosure to ensure that the EMI does not couple on the conductive wiring. These filters could be of passive components such as a combination of inductors and capacitors.

The term "RF detection system" interchangeably refers hereinafter to a system designed to detect and alert of the presence of predefined RF waves. This system will typically include a sensor such as an antenna, and an indicator.

The term "visual indicators" interchangeably refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "audible indicators" interchangeably refers hereinafter to a representation of sound, typically as an electrical voltage. Audible indicators have frequencies in the audio frequency range of roughly 20 to 20,000 Hz (the limits of human hearing). Audible indicators are either synthesized directly, or originate at a transducer such as a microphone, musical instrument pickup, phonograph cartridge, or tape head.

The term "sensible indicators" interchangeably refers hereinafter to a physical movement of at least a portion of the user interface, which is noticeable to the user (shaking, vibrating, quivering, etc.).

The term "placement" interchangeably refers hereinafter to a location for placing one or more medical equipment tubing. This is achieved by a mean such as a clip, anchor, catch, clasp, strip, nest, socket, dent, duct, channel, bridge, clamp, harness, concave shape, crater, gap, pocket, cavity, grip, belt, catch, snap, fastener, hook, hold, support, buckle, latch, lock, hasp, affixer, binder, joiner, band, ring, string, tie, link, chain, fastener, draw latch, lock, bolt, grip, bar, bond, clasp, connection, fixture, buckle, pin, peg, grapnel, band, pin, insertion, etc.

The term "connected" in reference to the MRD, closure assembly, and conduit parts and modules, interchangeably refers hereinafter to any contact, relation, association, integration, interconnection, joining, inserting, sewing, welding, interweaving, placing, nesting, layering, etc., of the closure assembly parts to each other and to a third party.

The term "plurality" interchangeably refers hereinafter to an integer a, when a>1.

The term "hinge" interchangeably refers hereinafter to any connection in which one part is movable in respect to the other. The parts could be connected by a flexible mechanism or material, joint, hook, thread, axis, juncture, turning point, fold, bend, elbow, knee, corner, fork, axis, pole, pivot, ball and socket, condyloid joint, mechanical device, hinge, barrel hinge, pivot hinges, double-acting floor hinge, butt/mortise hinges, case hinges, continuous hinges, piano hinges, concealed hinges, cup hinge, euro hinge, butterfly hinges, parliament hinge, flag hinges, strap hinges, H hinges, HL hinges, counter-flap hinge, flush hinge, coach hinge, rising butt hinge, double action spring hinge, tee hinge, friction hinge, security hinge, cranked hinge, storm-proof hinge, lift-off hinge, self-closing hinge, butt hinge, etc.

The term "automatic" in respect to the movement of a part of the shutting assembly interchangeably refers herein after to a pre-defined movement having a start location and an end location. Further this movement could be derived from an engine, a self-sliding movement when latching mechanism is released, pneumatic mechanism (compressed from the self-sliding movement downwards), hydraulic cylinder, using a gear shift system, etc.

The term "manual" in respect to the movement of a part of the shutting assembly interchangeably refers herein after to any application of force by the handler aimed at moving at least a portion of the moving part. This force is generated by an action such as pushing, pulling, lifting, levering, turning, twisting, hitting, lowering, etc.

The term "emergency release mechanism", interchangeably refers hereinafter to a mechanism used in immediate need of extracting a patient from the MRD bore that allows in one step the dislocation of at least a portion of the closure assembly providing access to the patient.

The term "remote control mechanism" interchangeably refers herein after to a component used for operating the device wirelessly from a short line-of-sight distance. This is operable by a means such as Bluetooth connectivity, motion sensor control, voice control, RF, infrared, ultrasonic, etc.

According to one embodiment of the present invention, in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding conduit (RFSC), having apertures shaped to permit passage of medical equipment tubing from the external environment of the MRD to inner space of the bore, affixed to the closure assembly, wherein the conduit is characterized by a length (l) and width (w), l:w ratio is greater than a predefined value n, thereby providing RF shielding.

According to another embodiment of the present invention the closure assembly is as depicted in the Utility model No. DE 202012104183 U1 dated 31, Oct. 2012 titled: a protective cover for MRI, and is incorporated in its entirety, as a reference.

According to another embodiment of the invention, an RFSC as defined above is disclosed, wherein the RFSC is adapted by means of size and shape to permit passage of medical equipment tubing, from inner space of said MRD bore to the external environment.

According to another embodiment of the invention, an RFSC as defined above is disclosed, wherein the RFSC is connected in a non-protruding manner to the closure assembly, thereby indirect access is provided between the MRD bore and the external environment.

According to another embodiment of the invention, an RFSC as defined above is disclosed, wherein the RFSC is shaped to permit passage of the medical equipment tubing having a plurality of shapes and sizes.

According to another embodiment of the invention, an RFSC as defined above is disclosed, wherein the RFSC further comprises at least one designated placement for passing the medical equipment tubing.

According to another embodiment of the invention, an RFSC as defined above is disclosed, wherein the RFSC profile along the width is of a shape selected from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the invention, an RFSC as defined above is disclosed, comprising an RFSC wall along the length, wherein the wall is of a shape selected from a group consisting of: straight, curved, polygonal, symmetrical, non-symmetrical and any combination thereof.

According to another embodiment of the invention, an RFSC as defined above is disclosed, wherein the cutouts are of a shape selected from a group consisting of: open shape, closed shape, polygon, circle, symmetrical, non-symmetrical, and any combination thereof.

According to another embodiment of the invention, an RFSC as defined above is disclosed, wherein at least a portion of the RFSC aperture comprise a curved edge profile; further wherein at least a portion of the RFSC is of a smoothed finish. Having a smooth finish or the like reduces the friction of the tubing against the conduit when moved against. This allows for less tubing rapture, and eases the placement and further manipulation of the tubes in the conduit.

According to another embodiment of the invention, an RFSC as defined above is disclosed, wherein at least a portion of the RFSC is perforated, further wherein the perforations are of a length and diameter configured as a waveguide with a cutoff frequency selected from a group consisting of: 0 to about 1000 MHz, 0 to about 500 MHz, 0 to about 200 MHz or the like as needed to meet the frequency of a specific MRD, and the frequency of EMI generated externally. These holes in the closure assembly are made to allow ventilation and light penetration in an otherwise closed space.

According to another embodiment of the invention, a RFSC as defined above is disclosed, wherein the RFSC has RF attenuation properties. These attenuation properties are reached by constructing the conduit as a waveguide whereas the RF is below the waveguide cutoff Further an RF filter can be installed defined to block RF of defined range. RF filters would provide protection to electrical power, data cables, etc. These RF filters permit the passage of electrical wiring thereby maintaining the RF shielding.

According to another embodiment of the invention, an RFSC as defined above is disclosed, wherein the RFSC is constructed as a detachable module. This module is then able to attach to other designated locations for example a specially designed port at a patient's bed, operating table, gurney, wheelchair, etc. In this manner no detachments and attachments of medical equipment tubing are necessary when transferring the patient to different placements.

According to another embodiment of the invention, an RFSC as defined above is disclosed, wherein at least a portion of the RFSC comprises electromagnetic conductive material.

According to another embodiment of the invention, an RFSC as defined above is disclosed, wherein the RFSC further comprises at least a portion of transparent material. Further the transparent material enables view of at least a portion of the patient. In other embodiments the transparent portion allows light to enter the MRD bore covered by the closure assembly.

According to another embodiment of the invention, an RFSC as defined above is disclosed, where at least a portion of the closure assembly is made of high endurance to impact materials. Such materials are composed from materials such as metal, metal alloys, composite materials and combination thereof. These composites are such as GFRP (glass-fiber reinforced plastic) and CFRP (carbon-fiber reinforced plastic).

According to another embodiment of the invention, an RFSC as defined above is disclosed, comprising a longitudinal axis wall along the length, and at least two walls perpendicular to the longitudinal axis wall, wherein at least one of the walls is maneuverably connected to the longitudinal wall remaining in a fixed position. This embodiment enables to hold the position of the medical equipment tubing within the conduit by maneuvering one of the walls in respect to the other to narrow the space of the conduit as long as the conduit is still characterized by a length (l) and width (w), l:w ratio is greater than a predefined value n, thereby providing RF shielding.

According to another embodiment of the invention, an RFSC as defined above is disclosed, comprising at least one telescopic wall, wherein the wall allows change of the width, length, or depth as long as the ratio between the width and the length of the conduit remains greater than a predefined value n. This embodiment further provides extra space for medical equipment tubing. In addition, this mechanism serves to hold the position of the tubing within the conduit.

According to another embodiment of the invention, an RFSC as defined above is disclosed, wherein the RFSC further comprises an RF detector system, further wherein the RF detection system comprises indicators selected from a group consisting of: audible, sensible, visual and any combination thereof.

According to another embodiment of the invention, an RFSC as defined above is disclosed, wherein the RFSC is affixed to the closure assembly at a location of at least a portion of the perimeter between the closure assembly and the MRD.

According to another embodiment of the invention, an RFSC as defined above is disclosed, wherein the RFSC further comprises an open face along the length, thereby enabling removal of the medical equipment tubing without detaching it from any of the equipment ends.

According to another embodiment of the invention, an RFSC as defined above is disclosed, wherein the conduit is configured to attenuate the passage of frequencies selected from a group consisting of: 0 to about 1000 MHz, 0 to about 500 MHz, 0 to about 200 MHz and any combination thereof.

According to another embodiment of the invention, an RFSC as defined above is disclosed, wherein the conduit is configured to attenuate electromagnetic interference by means selected from a group consisting of: waveguide, RF filter, waveguide filter, attenuating material, and any combination thereof.

According to another embodiment of the invention, an RFSC as defined above is disclosed, wherein at least a portion of the RFSC comprises shielding selected from a group consisting of: magnetic shielding, RF shielding, physical shielding and any combination thereof.

According to another embodiment of the invention, a RFSC as defined above is disclosed,
wherein the RFSC together with the closure assembly acts as a passive electromagnetic shield. In order to create an effective non-active magnetic shielding at least a portion of the closure assembly is constructed from magnetic alloys with high permeability and low coercivity such as Permalloy, and different types of Mu-metal. These are constructed from elements such as metal sheet, metal casting, metal screen, metal containing foam, metallic ink and any combination thereof.

According to another embodiment of the invention, an RFSC as defined above is disclosed, wherein the at least a portion of the RFSC, the outer structure of the MRD, the closure assembly or any combination thereof, form a conductive circuit. This could be formed with the existing MRD or with another element surrounding the MRD. This arrangement will serves as an electromagnetic shield. Further wherein at least a portion of the closure assembly, and the surrounding elements, are typically made of metal such as copper, galvanized steel, aluminum etc.

According to another embodiment of the invention, an RFSC as defined above is disclosed, wherein the RFSC is affixed to the closure assembly further comprising a hinge having at least one first connecting member connected to the MRD and at least one second connecting member, connected to the closure assembly, further wherein at least one first connecting member is maneuverably coupled to at least one second connecting member.

According to another embodiment of the invention, an RFSC as defined above is disclosed, wherein the hinge further comprises an emergency release mechanism, thereby enabling detachment of at least one hinged connected member.

According to another embodiment of the invention, an RFSC as defined above is disclosed, wherein the hinge member connected to the MRD is connected at a location selected from a group consisting of: at least a portion of the MRD external wall, within at least a portion of the MRD bore, at least a portion of the MRD aperture perimeter and any combination thereof.

According to another embodiment of the invention, an RFSC as defined above is disclosed, wherein the hinge member connected to the MRD is connected at a location, in reference to the MRD aperture, selected from a group consisting of: above, below, right, left, perpendicular to the floor, not perpendicular to the floor and any combination thereof.

According to another embodiment of the invention, an RFSC as defined above is disclosed, wherein the hinge connecting members are connected in a manner selected from a group consisting of: directly, indirectly and any combination thereof.

According to another embodiment of the invention, an RFSC as defined above is disclosed, wherein at least one hinge connecting member is maneuverable by a mean selected from a group consisting of: manual, automatic, self, remote control and any combination thereof.

According to one embodiment of the present invention, in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding hinge (RFSH) comprising at least one first connecting member connected to the MRD or open bore thereof and at least one second connecting member, connected to the closure assembly; at least one first connecting member is maneuverably coupled to at least one second connecting member; comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the invention, an RFSH as defined above is disclosed, wherein the RFSH member connected to the MRD is connected at a location selected from a group consisting of: at least a portion of the MRD external wall, within at least a portion of the MRD bore, at least a portion of the MRD aperture perimeter and any combination thereof.

According to another embodiment of the invention, an RFSH as defined above is disclosed, wherein the hinged first connecting member is connected at a location, in respect to the MRD aperture, selected from a group consisting of: left, right, below, above and any combination thereof.

According to another embodiment of the invention, an RFSH as defined above is disclosed, wherein the hinged first connecting member is connected to the MRD in a manner selected from a group consisting of: directly, indirectly and any combination thereof. In this embodiment the hinge connecting members could further be supported by additional elements such as bars, rods, sheets, wires etc. to support the connection and to assist in dividing the weight load of the closure assembly.

According to another embodiment of the invention, an RFSH as defined above is disclosed, wherein the at least one hinge connecting member is maneuverable by a mean selected from a group consisting of: manual, automatic, self, remote control and any combination thereof.

According to another embodiment of the invention, an RFSH as defined above is disclosed, wherein at least a portion of the RFSH comprises a material selected from a group consisting of: diamagnetic, paramagnetic, ferromagnetic materials and combination thereof.

According to another embodiment of the invention, an RFSH as defined above is disclosed, wherein the RFSH is adapted by means of size and shape to permit passage of the medical equipment tubing, from the inner space of the MRD bore to the external environment and contrariwise.

According to another embodiment of the invention, an RFSH as defined above is disclosed, wherein the RFSH is shaped to permit passage of the medical equipment tubing having a plurality of shapes and sizes.

According to another embodiment of the invention, an RFSH as defined above is disclosed, wherein the RFSH further comprising at least one designated placement for passing the medical equipment tubing.

According to another embodiment of the invention, an RFSH as defined above is disclosed, wherein at least a portion of the RFSH aperture comprise a curved edge profile.

According to another embodiment of the invention, an RFSH as defined above is disclosed, wherein at least a portion of the RFSH is of a smoothed finish.

According to another embodiment of the invention, an RFSH as defined above is disclosed, comprising an emergency release mechanism, wherein the mechanism enables detachment of at least one the hinged connected member.

According to another embodiment of the invention, an RFSH as defined above is disclosed, wherein at least a portion of the RFSH comprises shielding selected from a group consisting of: magnetic shielding, RF shielding, physical shielding and any combination thereof.

According to another embodiment of the invention, an RFSH as defined above is disclosed, wherein at least a portion of the RFSH comprises electromagnetic conductive material.

According to another embodiment of the invention, an RFSH as defined above is disclosed, wherein at least a portion of the RFSC comprises transparent material.

According to another embodiment of the invention, an RFSH as defined above is disclosed, wherein the conduit further comprising an RF detector system, further wherein the RF detection system comprises indicators selected from a group consisting of: audible, sensible, visual and any combination thereof.

According to another embodiment of the invention, an RFSH as defined above is disclosed, wherein the conduit is configured to attenuate the passage of frequencies selected from a group consisting of: 0 to about 1000 MHz, 0 to about 500 MHz, 0 to about 200 MHz and any combination thereof.

According to another embodiment of the invention, an RFSH as defined above is disclosed, wherein the conduit is configured to attenuate electromagnetic interference by means selected from a group of: waveguide, RF filter, waveguide filter, attenuating material, and any combination thereof.

According to another embodiment of the invention, an RFSH as defined above is disclosed, wherein at least a portion of the RFSH closes an electromagnetic conductive circuit with the closure assembly.

According to another embodiment of the invention, a method for RF shielding an MRD from its external environment generated EMI, and RF shielding the external environment from the MRD generated EMI, comprising steps of: (a) obtaining an MRD comprising: (i) a main longitudinal axis with a distal and proximal ends; (ii) an open bore extended along the axis and terminated by an aperture located in the proximal end; and (iii) a closure assembly shaped to fit the aperture comprising at least one conduit having apertures shaped to permit passage of medical equipment tubing from the external environment of the MRD to inner space of the bore, affixed to the closure assembly; (b) installing the closure assembly comprising the conduit; (c) inserting patient into the MRD bore; (d) passing the medical equipment tubing through the conduit; (e) covering the MRD bore with the closure assembly; and (f) imaging patient, wherein the conduit is characterized by a length (l) and width (w), l:w ratio is greater than a predefined value n, thereby providing RF shielding.

According to another embodiment of the invention, a method as defined above is disclosed, additionally comprising a step of connecting the conduit in a non-protruding manner to the closure assembly, thereby indirect access is provided between the MRD bore and the external environment.

According to another embodiment of the invention, a method as defined above is disclosed, additionally comprising a step of connecting at least one designated placement for passing the medical equipment tubing within the conduit.

According to another embodiment of the invention, a method as defined above is disclosed, additionally comprising a step of connecting the RFSC constructed as a detachable module.

According to another embodiment of the invention, a method as defined above is disclosed, additionally comprising a step of connecting an RF detector system, further selecting the RF detection system indicators from a group consisting of: audible, sensible, visual and any combination thereof.

According to another embodiment of the invention, a method as defined above is disclosed, additionally comprising a step of obtaining a conduit comprising at least one telescopic wall.

According to another embodiment of the invention, a method as defined above is disclosed, additionally comprising a step of changing the wall width, length, or depth as long as the ratio between the width and the length of the conduit remains greater than a predefined value n.

According to another embodiment of the invention, a method as defined above is disclosed, additionally comprising a step of obtaining the RFSC comprising an open face along the length, According to another embodiment of the invention, a method as defined above is disclosed, additionally comprising a step of installing or removing the medical equipment tubing without detaching it from any of the equipment ends.

According to another embodiment of the invention, a method as defined above is disclosed, wherein the RFSC is affixed to a closure assembly further comprising a hinge having at least one first connecting member connected to the MRD and at least one second connecting member, connected to the closure assembly, further wherein the at least one first connecting member is maneuverably coupled to the at least one second connecting member.

According to another embodiment of the invention, a method as defined above is disclosed, additionally comprising a step of emergency releasing the patient by detaching of at least one the hinged connected member.

According to another embodiment of the invention, a method as defined above is disclosed, additionally comprising a step of maneuvering at least one the hinge connecting member by a mean selected from a group consisting of: manual, automatic, self, remote control and any combination thereof.

According to another embodiment of the invention, a method as defined above is disclosed, additionally comprising a step of obtaining an RF shielding hinge (RFSH) comprising at least one first connecting member connected to the MRD and at least one second connecting member, connected to the closure assembly; the at least one first connecting member is maneuverable coupled to the at least one second connecting member, comprising a conduit, having apertures shaped to permit passage of medical equipment tubing from the external environment of the MRD to inner space of the bore;

It is another object of the current invention to disclose a method as described above, additionally comprising a step of maneuvering at least one the hinge connecting member by a mean selected from a group consisting of: manual, automatic, self, remote control and any combination thereof.

According to another embodiment of the invention, a method as defined above is disclosed, additionally comprising a step of connecting at least one designated placement for passing the medical equipment tubing to the RFSH.

According to another embodiment of the invention, a method as defined above is disclosed, additionally comprising a step of emergency releasing the patient by detaching of at least one the hinged connected member.

According to another embodiment of the invention, a method as defined above is disclosed, additionally comprising a step of connecting an RF detector system, further selecting RF detection system indicators form a group consisting of: audible, sensible, visual and any combination thereof.

According to another embodiment of the invention, a method for manufacturing an RF shielding conduit (RFSC) in an MRD closure assembly comprising steps of: (a) obtaining a closure assembly shaped to fit an aperture of an MRD bore; (b) defining dimensions of the RFSC a length (l) and width (w), so that l:w ratio is greater than a predefined value n\ (c) defining dimensions of the RFSC to permit passage of medical equipment tubing within; (d) defining the location of the RFSC within the closure assembly to enable access to the handler; (e) forming defined the RFSC; and (f) connecting the RFSC to the closure assembly, wherein, the closure assembly comprises a conduit having a longitudinal axis, comprising a proximal end having a cutout facing the MRD bore, and a distal end having a cutout facing environment external of the MRD.

According to another embodiment of the invention, a method as defined above is disclosed, additionally comprising a step of adapting the RFSC is by means of size and shape to permit passage of the medical equipment tubing, from inner space of the MRD bore to the external environment.

According to another embodiment of the invention, a method as defined above is disclosed, additionally comprising a step of connecting the RFSC in a non-protruding manner to the closure assembly, thereby providing indirect access between the MRD bore and the external environment.

According to another embodiment of the invention, a method as defined above is disclosed, additionally comprising a step of shaping the RFSC to permit passage of the medical equipment tubing having a plurality of shapes and sizes.

According to another embodiment of the invention, a method as defined above is disclosed, additionally comprising a step of designing at least one designated placement for passing the medical equipment tubing within the RFSC.

According to another embodiment of the invention, a method as defined above is disclosed, additionally comprising a step of selecting RFSC profile along the width is from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the invention, a method as defined above is disclosed, additionally comprising a step of selecting an RFSC wall shape along the longitudinal axis, from a group consisting of: straight, curved, polygonal, symmetrical, non-symmetrical and any combination thereof.

According to another embodiment of the invention, a method as defined above is disclosed, additionally comprising a step of forming at least a portion of the RFSC aperture comprising a curved edge profile.

According to another embodiment of the invention, a method as defined above is disclosed, additionally comprising a step of forming at least a portion of the RFSC in a smoothed finish.

According to another embodiment of the invention, a method as defined above is disclosed, additionally comprising a step of perforating the RFSC, further the perforations are of a length and diameter configured as a waveguide to attenuate RF selected from a group consisting of: 0 to about 1000 MHz, 0 to about 500 MHz, 0 to about 200 MHz and any combination thereof.

According to another embodiment of the invention, a method as defined above is disclosed, additionally comprising a step of constructing the RFSC as a detachable module.

According to another embodiment of the invention, a method as defined above is disclosed, additionally comprising a step of making at least a portion of the RFSC comprising electromagnetic conductive material.

According to another embodiment of the invention, a method as defined above is disclosed, additionally comprising a step of making at least a portion of the RFSC comprising transparent material.

According to another embodiment of the invention, a method as defined above is disclosed, additionally comprising a step of defining the RFSC comprising a longitudinal axis wall, and at least two walls perpendicular to the longitudinal axis wall, further at least one of the walls is maneuverably connected to the longitudinal wall remaining in a fixed position.

According to another embodiment of the invention, a method as defined above is disclosed, additionally comprising a step of connecting an RF detector system, further selecting the RF detection system indicators from a group consisting of: audible, sensible, visual and any combination thereof.

According to another embodiment of the invention, a method as defined above is disclosed, additionally comprising a step of defining at least one conduit telescopic wall, allowing change of the width, length, or depth as long as the ratio between the width and the length of the conduit remains greater than a predefined value n.

According to another embodiment of the invention, a method as defined above is disclosed, additionally comprising a step of affixing the RFSC to the closure assembly at a location of at least a portion of the perimeter between the closure assembly and the MRD.

According to another embodiment of the invention, a method as defined above is disclosed, additionally comprising a step of defining the RFSC further comprising an open face along the length, thereby enabling removal of the medical equipment tubing without detaching it from any of the equipment ends.

According to another embodiment of the invention, a method as defined above is disclosed, additionally comprising a step of configuring the conduit to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring the conduit to attenuate electromagnetic interference by means selected from a group of: waveguide, RF filter, waveguide filter, attenuating material, and any combination thereof.

According to another embodiment of the invention, a method as defined above is disclosed, additionally comprising a step of making at least a portion of the RFSC comprising shielding selected from a group consisting of: magnetic shielding, RF shielding, physical shielding and any combination thereof.

According to another embodiment of the invention, a method as defined above is disclosed, additionally comprising a step of forming at least a portion of the RFSC in a shape closing a conductive circuit with the closure assembly.

According to another embodiment of the invention, a method as defined above is disclosed, additionally comprising a step of affixing the RFSC to a closure assembly further comprising a hinge having at least one first connecting member connected to the MRD and at least one second connecting member, connected to the closure assembly, further wherein the at least one first connecting member is maneuverably coupled to the at least one second connecting member.

According to another embodiment of the invention, a method as defined above is disclosed, additionally comprising a step of including an emergency release mechanism to the hinge, thereby enabling detachment of at least one the hinged connected member.

According to another embodiment of the invention, a method as defined above is disclosed, additionally comprising a step of selecting the location of the connection between the hinge member to the MRD from a group consisting of: at least a portion of the MRD external wall, within at least a portion of MRD bore, at least a portion of the MRD aperture perimeter and any combination thereof.

According to another embodiment of the invention, a method as defined above is disclosed, additionally comprising a step of selecting the location, in reference to the MRD aperture, of the connection between the hinge member to the MRD from a group consisting of: above, below, right, left, perpendicular to the floor, not perpendicular to the floor and any combination thereof.

According to another embodiment of the invention, a method as defined above is disclosed, additionally comprising a step of connecting the hinge connecting members in a manner selected from a group consisting of: directly, indirectly and any combination thereof.

According to another embodiment of the invention, a method as defined above is disclosed, additionally comprising a step of selecting a mean of maneuvering at least one the hinge connecting member from a group consisting of: manual, automatic, self, remote control and any combination thereof.

According to another embodiment of the invention, a method as defined above is disclosed, additionally comprising a step of defining the conduit in at least a portion of an RF shielding hinge (RFSH), having at least one first connecting member connected to the MRD and at least one second connecting member, connected to the closure assembly; the at least one first connecting member is maneuverable coupled to the at least one second connecting member.

According to another embodiment of the invention, a method as defined above is disclosed, additionally comprising a step of connecting the RFSH member to the MRD at a location selected from a group consisting of: at least a portion of the MRD external wall, within at least a portion of MRD bore, at least a portion of the MRD aperture perimeter and any combination thereof.

According to another embodiment of the invention, a method as defined above is disclosed, additionally comprising a step of connecting the hinged first connecting member to the MRD at a location, in respect to the MRD aperture, selected from a group consisting of: left, right, below, above and any combination thereof.

According to another embodiment of the invention, a method as defined above is disclosed, additionally comprising a step of connecting the hinged first connecting member to the MRD in a manner selected from a group consisting of: directly, indirectly and any combination thereof.

According to another embodiment of the invention, a method as defined above is disclosed, additionally comprising a step of selecting a mean of maneuvering at least one the hinge connecting member from a group consisting of: manual, automatic, self, remote control and any combination thereof.

According to another embodiment of the invention, a method as defined above is disclosed, additionally comprising a step of forming at least a portion of the RFSH comprising a material selected from a group consisting of: diamagnetic, paramagnetic, ferromagnetic materials and combination thereof.

According to another embodiment of the invention, a method as defined above is disclosed, additionally comprising a step of adapting the RFSH by means of size and shape to permit passage of the medical equipment tubing, from the inner space of the MRD bore to the external environment.

According to another embodiment of the invention, a method as defined above is disclosed, additionally comprising a step of shaping the RFSH to permit passage of the medical equipment tubing having a plurality of shapes and sizes.

According to another embodiment of the invention, a method as defined above is disclosed, additionally comprising a step of designing at least one designated placement for passing the medical equipment tubing within the conduit.

According to another embodiment of the invention, a method as defined above is disclosed, additionally comprising a step of forming at least a portion of the RFSH aperture comprising a curved edge profile.

According to another embodiment of the invention, a method as defined above is disclosed, additionally comprising a step of forming at least a portion of the RFSH in a smoothed finish.

According to another embodiment of the invention, a method as defined above is disclosed, additionally comprising a step of including an emergency release mechanism wherein the mechanism enables detachment of at least one the hinged connected member.

According to another embodiment of the invention, a method as defined above is disclosed, additionally comprising a step of selecting shielding of at least a portion of the RFSH from a group consisting of: magnetic shielding, RF shielding, physical shielding and any combination thereof.

According to another embodiment of the invention, a method as defined above is disclosed, additionally comprising a step of forming at least a portion of the RFSH comprising electromagnetic conductive material.

According to another embodiment of the invention, a method as defined above is disclosed, additionally comprising a step of forming at least a portion of the RFSC comprising transparent material.

According to another embodiment of the invention, a method as defined above is disclosed, additionally comprising a step of connecting an RF detector system, further selecting RF detection system indicators selected form a group consisting of: audible, sensible, visual and any combination thereof.

According to another embodiment of the invention, a method as defined above is disclosed, additionally comprising a step of configuring the RFSH to attenuate the passage of frequencies selected from a group consisting of: 0 to about 1000 MHz, 0 to about 500 MHz, 0 to about 200 MHz and any combination thereof.

According to another embodiment of the invention, a method as defined above is disclosed, additionally comprising a step of configuring to attenuate electromagnetic interference by means selected from a group of: waveguide, RF filter, waveguide filter, attenuating material, and any combination thereof.

According to another embodiment of the invention, a method as defined above is disclosed, additionally comprising a step of forming at least a portion of the RFSC in a shape closing an electromagnetic conductive circuit with the closure assembly.

According to another embodiment of the invention, a standard of care protocol is disclosed for magnetic resonance imaging a patient placed within MRD bore, connected to medical equipment, whilst not leaking RF into the MRD characterized by providing in a magnetic resonance imaging device (MRD) comprising (a) a main longitudinal axis with a distal and proximal ends; (b) an open bore extended along the axis and terminated by an aperture located in the proximal end; and (c) a closure assembly which is shaped to fit the aperture; an RF shielding conduit (RFSC), having apertures shaped to permit passage of medical equipment tubing from the external environment of the MRD to inner space of the bore, affixed to the closure assembly, the conduit is characterized by a length (l) and width (w), l:w ratio is greater than a predefined value n, thereby providing RF shielding, wherein at least one of the following is held true: (a) the average number of MRD associated patient's health complications when utilizing the RFSC is n times lower than the average number of patient's MRI associated health complications, n is equal or greater than 1.05; (b) the average number of insurable claims of a selected from a group consisting of: manufacturer, handler, user, operator, medical care personal, medical facility, medical facility management or any combination thereof when utilizing the RFSC is m times lower than patient MRI associated insurable claims; m is equal or greater than 1.05; (c) the average number of repeated MRI due to EMI when utilizing the RFSC is p times lower than the average number of repeated MRI; p is equal or greater than 1.05; (d) the average number of misinterpreted MRI due to EMI produced artifacts when utilizing the RFSC is o times lower than the average number of repeated MRI; o is equal or greater than 1.05; (e) the average number of patients detached from medical equipment during MRI when utilizing the RFSC is z times lower than the average number patients detached from medical equipment during MRI; z is equal or greater than 1.05; and (f) the average number of patient's health complications due to EMI interfering with medical equipment is u times higher than when utilizing the RFSC assembly; u is equal or greater than 1.05.

Reference is now made to FIG. 1A schematically illustrating, in an out of scale manner, an embodiment of the invention. An illustration of an MRD (800) connected to a closure assembly (200) in a rectangular embodiment for shutting the entrance of an MRD bore (101) presented in its closed configuration. The closure assembly further harboring an RF shielding conduit having cutouts (60, 50) shaped to permit passage of medical equipment tubing. Further, the conduit is shaped to enable passing of, for example, life support tubing and monitors' sensors from the outer side of the MRD into the inner side of the MRD and contrariwise of different sizes and shapes. In some embodiments of the present invention a closure assembly comprises a part such as a panel, lid, shutter, door, leaf, semi permeable web, bars, etc. (200).

Reference is now made to FIG. 1B schematically illustrating, in an out of scale manner, an embodiment of the invention. The rectangular embodiment of a closure assembly (200) is inserted into a multifaceted shaped embodiment of an RF shielding conduit (104). In this embodiment the conduit has two exits (65, 66) enabling threading of medical equipment tubing to different vectors at the MRD external environment.

Reference is now made to FIG. 1C schematically illustrating, in an out of scale manner, an embodiment of the invention. An inside view, presenting a rectangular embodiment of the closure assembly (200) including a conduit of a multifaceted shape (104).

Figure 1E:
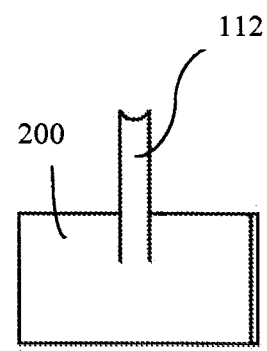
FIG. 1E is a schematic illustration, in an outside view, of a closure assembly in a rectangular embodiment comprising a conduit of a cylindrical shape.
Figure 1F:
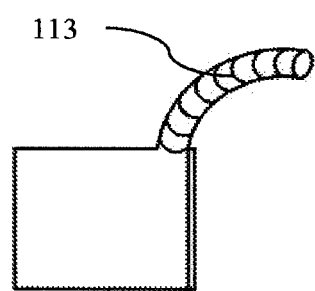
FIG. 1F is a schematic illustration, in an outside view, of a closure assembly in a rectangular embodiment comprising a conduit placed on the upper part.
Figure 1G:
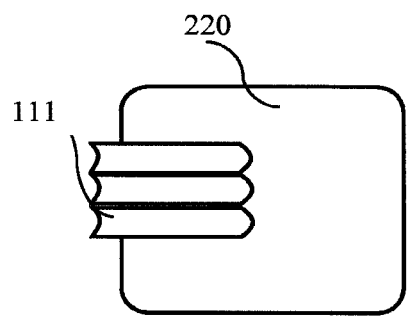
FIG. 1G is a schematic illustration, in an outside view, of a closure assembly in a rectangular embodiment comprising a plurality of conduits of a cylindrical shape.

Reference is now made to FIG. 1D-G schematically illustrating, in an out of scale manner, various embodiments of the RF shielding conduit in a closure assembly. The closure assembly is positioned at the proximal aperture of the MRD bore, to enable covering the aperture while the conduit maintains passage from within the MRD bore to the external environment for the tubing, cables, devices, sensors, etc., involved in medical equipment and physical conditions monitoring and support. In FIG. 1D a closure assembly is illustrated in a circular embodiment (210) comprising a conduit of a cylindrical shape (106) is presented. In FIG. 1E a closure assembly is illustrated in a rectangular embodiment (200) comprising a conduit of a cylindrical shape (112) exiting from approximately the middle of the closure assembly; the conduit is placed at the left, right, within, top, bottom, and any combination thereof of the closure assembly. In FIG. 1F a closure assembly is illustrated in a rectangular embodiment (200) comprising a conduit connecting to the upper contour of the closure assembly; the conduit is a flexible, telescopic or rigid tube (113). In FIG. 1G a closure assembly is illustrated in a rectangular embodiment (220) comprising a plurality of conduits (111) of a cylindrical shape.

Figure 2A:
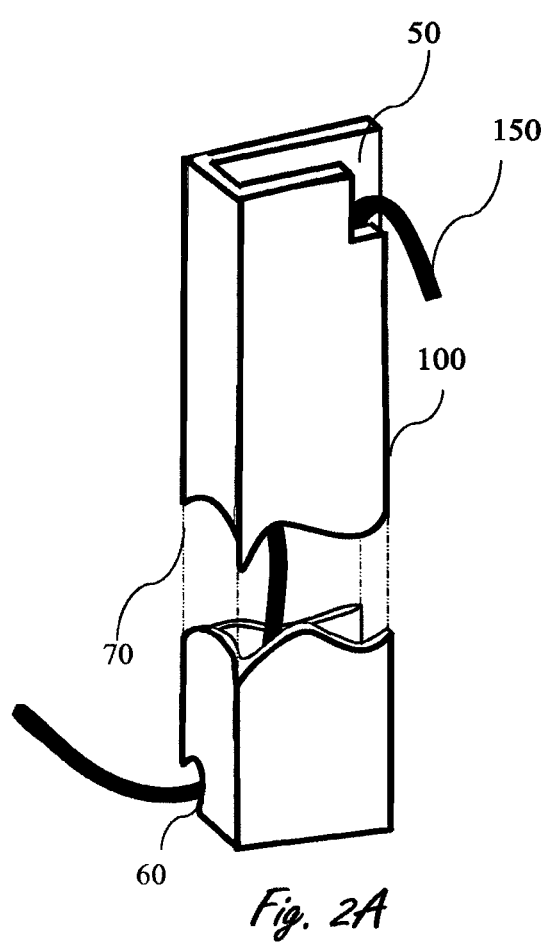
FIG. 2A is a schematic illustration of an embodiment of a conduit (100)

Reference is now made to FIG. 2A schematically illustrating, in an out of scale manner, an embodiment of the invention presenting a conduit (100) constructed of a multi faced hollow U-shaped frame, that has a cutout face on one side. Further in this embodiment the conduit includes a rectangular opening facing the MRD bore (50) and another circular opening in (60) facing the exterior of the MRD bore. These cutouts are of a shape such as rectangular, circular, elliptical, symmetrical, non-symmetrical, etc. An exemplary tube (150) is passed through the conduit via the cutouts. The conduit is has designated placements for positioning each tube, whereas these placements are labeled to assist in locating a specific tube (not shown). In some embodiments the tubes are placed and locked into position with a mean such as a cable anchor or strip (not shown). In some embodiments the tube is placed without a designated placement label or hold (FIG. 2A). In some embodiments the tube is passed directly through the bottom opening of a conduit without a designated cutout. Further the overall length (70) of the conduit is varied as long as the ratio between length (l) and width (w) is greater than a predefined value n.

Figure 2B:
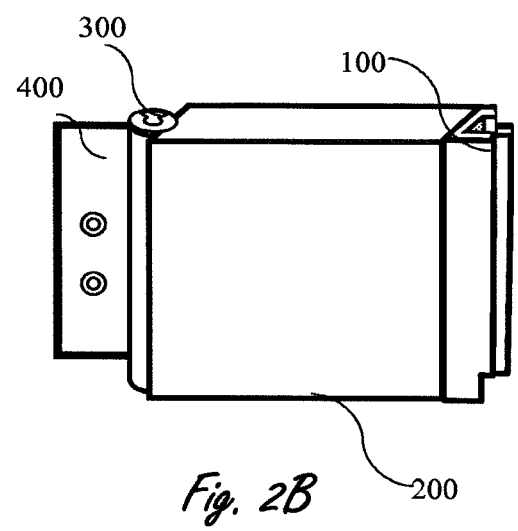
FIG. 2B is a schematic illustration, in an outside view, of a closure assembly, illustrating an arrangement where a conduit is connected along the side contour of a rectangular embodiment of a closure assembly; the hinge like structure is located on the opposite side connected to a second part fixed to an MRD

Reference is now made to FIG. 2B schematically illustrating, in an out of scale manner, an embodiment of the invention. An arrangement is presented, in an outside view, of a closure assembly (200), where a conduit (100) is connected along the side contour of a rectangular embodiment of a closure assembly; the hinge like structure (300) is located on the opposite side connected to a second part (400) fixed to an MRD. The part fixed to the MRD is connected by a mean such as screw, bolt, spike, pin, sliding bar, staple, nail, adhesive, belt, harness, etc. This hinge is connected directly or indirectly to a location selected from a group consisting of: MRD wall, within MRD bore, a portion of the closure assembly and any combination thereof. Further, the conduit (100) is connected to the side contour of the closure assembly (200). In this embodiment the conduit is placed at a location along a portion of the perimeter between the closure assembly and the MRD bore. This embodiment enables the tubes and wires of the medical equipment to pass along the side of the closure so that during insertion and exertion of the patient there is no need to disconnect the tubing on either end. This embodiment further allows fast mobility of the patient when needed, while minimizing the stress to the patient caused by detaching him from medical support and monitoring.

Figure 2C:
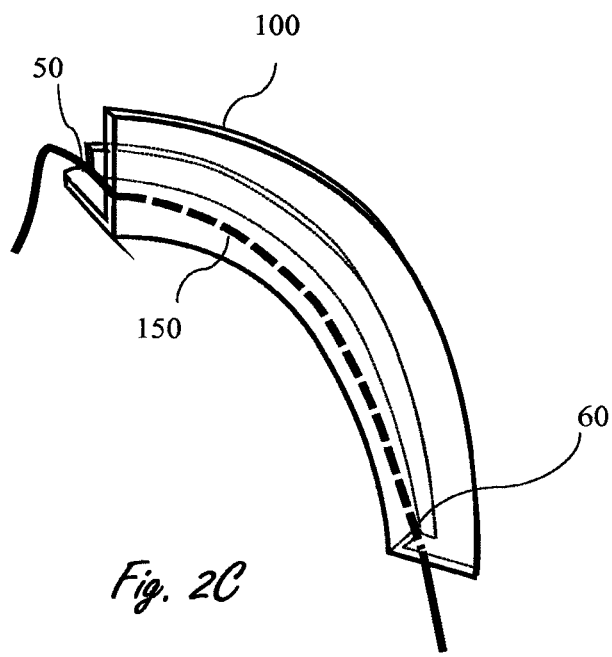
FIG. 2C is a schematic illustration of a curved embodiment of a conduit (100)

Reference is now made to FIG. 2C schematically illustrating, in an out of scale manner, an embodiment of the invention presenting an arch like conduit (100), having a U-shaped profile, with designated cutouts for entry (50) of an exemplary tube (150), and exiting out of a bottom opening (60). The conduit is fit for attaching to a circular embodiment of a closure assembly, along a portion of the border between the closure assembly and the MRD bore. This embodiment allows for insertion and extraction of the patient without threading the medical equipment tubing through, but only placing the tubing along the conduit in a manner that does not force disconnection of the tube on either side.

Figure 2D:
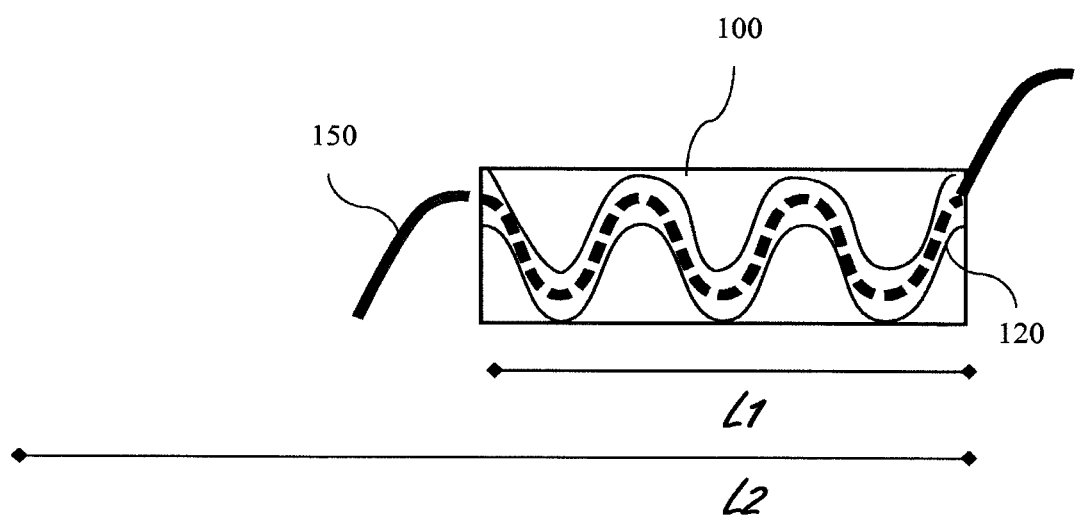
FIG. 2D is a schematic illustration, in a side view, of an embodiment of a conduit (100)

Reference is now made to FIG. 2D schematically illustrating, in an out of scale manner, an embodiment of the invention presenting a side view of an embodiment of a conduit (100). In this embodiment the conduit wall along its longitudinal axis is of a sinusoid wave shape (120). In this embodiment the tubing (150) is passed along an l2 distance that is longer than the external measured distance of /l. This embodiment allows for an overall shorter conduit to still maintain the ratio between length (l) and width (w) is greater than a predefined value n.

Reference is now made to FIG. 3A schematically illustrating, in an out of scale manner, an embodiment of the invention presenting an outside view, of an embodiment of an RF shielding hinge with a conduit (107). The hinge-like structure comprises a tracking conduit (107). The conduit is a waveguide configured by means of shape, size and material to attenuate EMI and to permit passage of medical equipment. The hinge-like structure is either of a cylindrical (107) or a multifaceted shape. The hinge is further connected to the closure assembly (200).

Reference is now made to FIG. 3B schematically illustrating, in an out of scale manner, an embodiment of the invention presenting an outside view, of an embodiment of a RF shielding hinge with a conduit (108) along a portion of the hinge. The hinge-like structure comprises a conduit (108) tracking only a portion of the hinge-like structure.

Reference is now made to FIG. 3C schematically illustrating, in an out of scale manner, an embodiment of the invention. In this embodiment an arrangement is presented, an MRD (800), having an open bore, covered by a closure assembly (200) connected to an RF shielding hinge (107), in a portion of which medical equipment tubing (150) is passed through from the external environment to the inner space of the MRD bore (202) where the patient is placed.

Figure 4A:
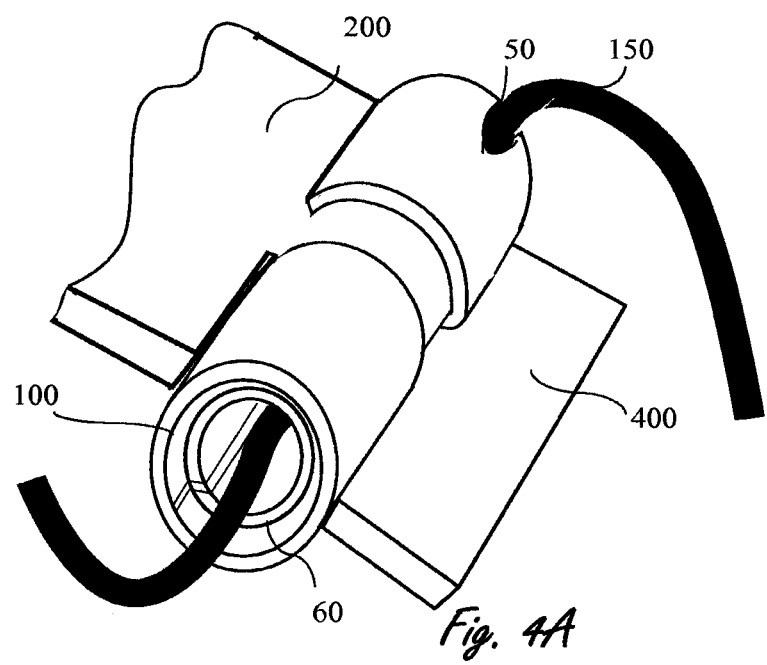

Reference is now made to FIG. 4A schematically illustrating, in an out of scale manner, an embodiment of the invention presenting a perspective view of an RF shielding hinge (100), comprising a conduit fitting for the passage of an exemplary tube (150) of medical equipment. In this embodiment the hinge has a first connecting member (200) connected to the closure assembly, and a second member connected to the MRD (400). The hinge enables maneuvering of the closure assembly in respect to the MRD. The tube is passed through an opening on one side of the hinge (60) into a hollow section within the hinge to exit in a fitted cutout aperture (50). In some embodiments there are apertures on both sides of the hinge in the entry and exit points of the tube. Further they can of a plurality of shapes and sizes. The conduit in which the medical equipment tubing are tunneled is characterized by a length (l) and width (w), l:w ratio is greater than a predefined value n, thereby providing RF shielding.

Figure 4B:
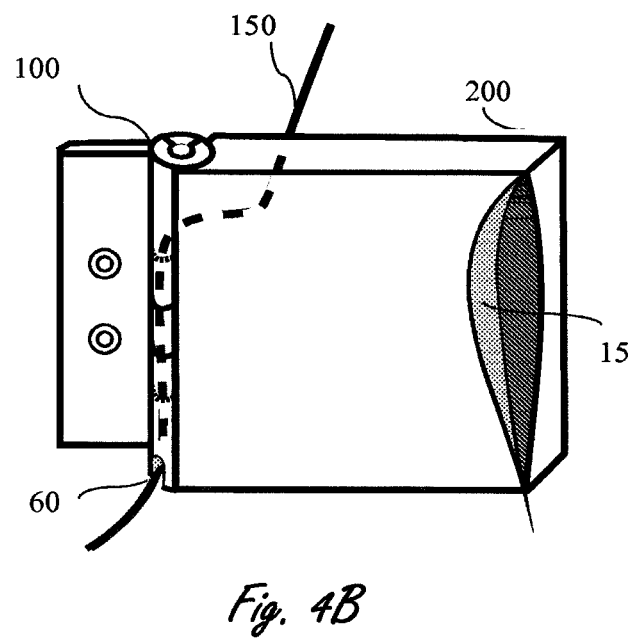
FIG. 4B is a schematic illustration presenting an embodiment of an RF shielding hinge (100), in a closure assembly, in which tubing is passed through a portion of the RF shielding hinge.

Reference is now made to FIG. 4B schematically illustrating, in an out of scale manner, an embodiment of the invention presenting an embodiment of an RF shielding hinge (100), one member is connected to a closure assembly (200), and another member is connected to the MRD. Medical equipment tubing (150) is passed through a portion of the RF shielding hinge. The closure assembly in this embodiment includes a handle (15).

Figure 5:
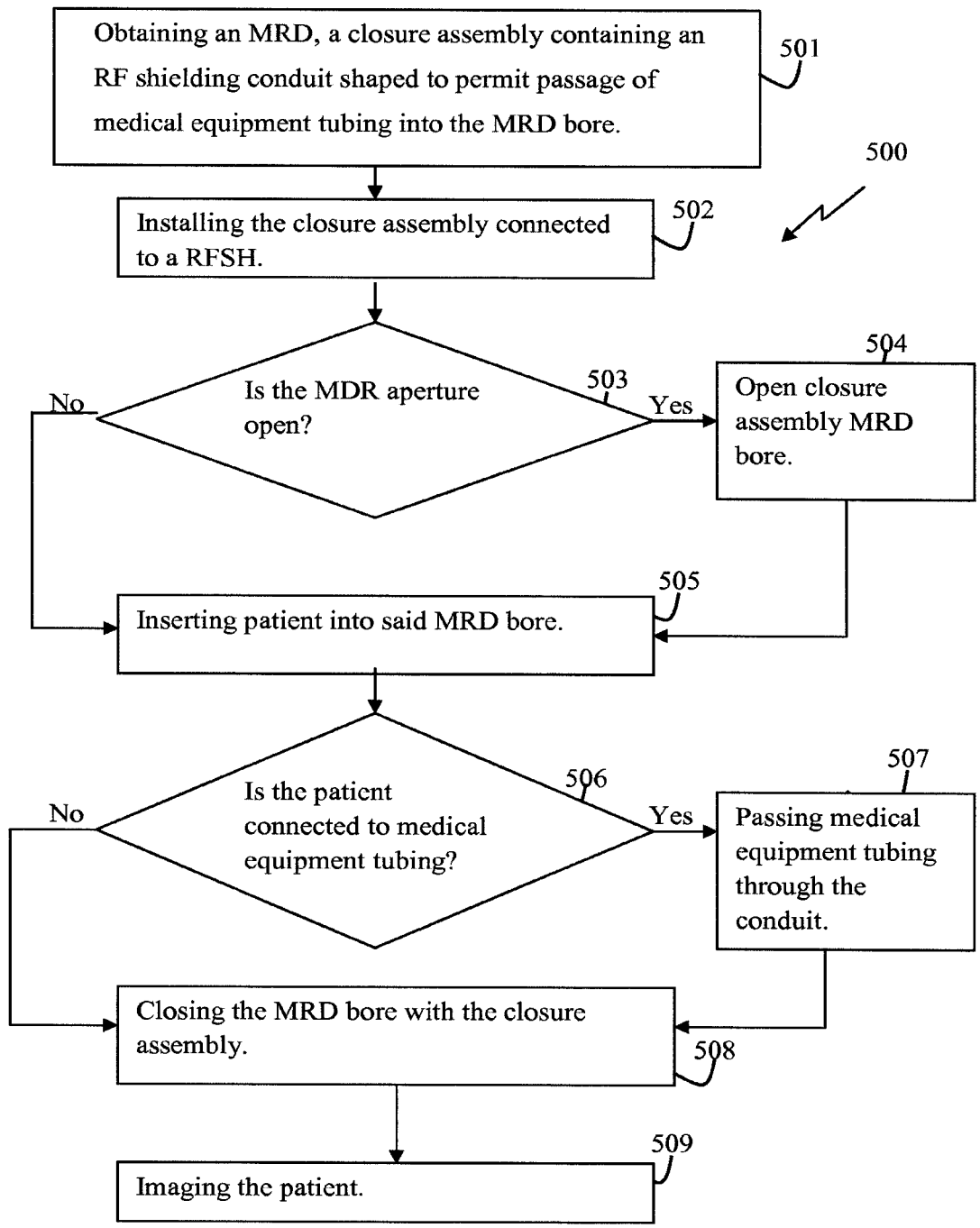
FIG. 5 is a schematic flowchart presenting a method of RF shielding an MRD from its external environment generated EMI, and RF shielding the external environment from the MRD generated EMI.

Reference is now made to FIG. 5 presenting a schematic flowchart (500) describing a method of RF shielding an MRD from its external environment generated EMI, and RF shielding the external environment from the MRD generated EMI. The first step (501) is obtaining an MRD having an open bore, and a closure assembly fitting to cover the open bore aperture. The closure assembly is one containing a conduit that is characterized by a length (l) and width (w), l:w ratio is greater than a predefined value n, thereby providing RF shielding. This RF shielding conduit comprises cutouts fitting to permit passage of medical equipment tubing within. Further this conduit is shaped to allow installation and passage of medical equipment tubing of various sizes and shapes into the MRD bore from the external environment and contrariwise. The next step (502) is installing the closure assembly having a conduit to the MRD. Following, if the MRD bore is open (503) insert the patient into the MRD bore (505). If closed, open the closure assembly first (504). If the patient is connected to medical equipment (506), the next step is to tunnel the medical equipment from the patient within the MRD bore through the RF shielding conduit to the external environment (507). Following, close the MRD bore with the closure assembly (508), while the patient is still connected to medical equipment tubing. The last step is to image the patient (509).

Figure 6:
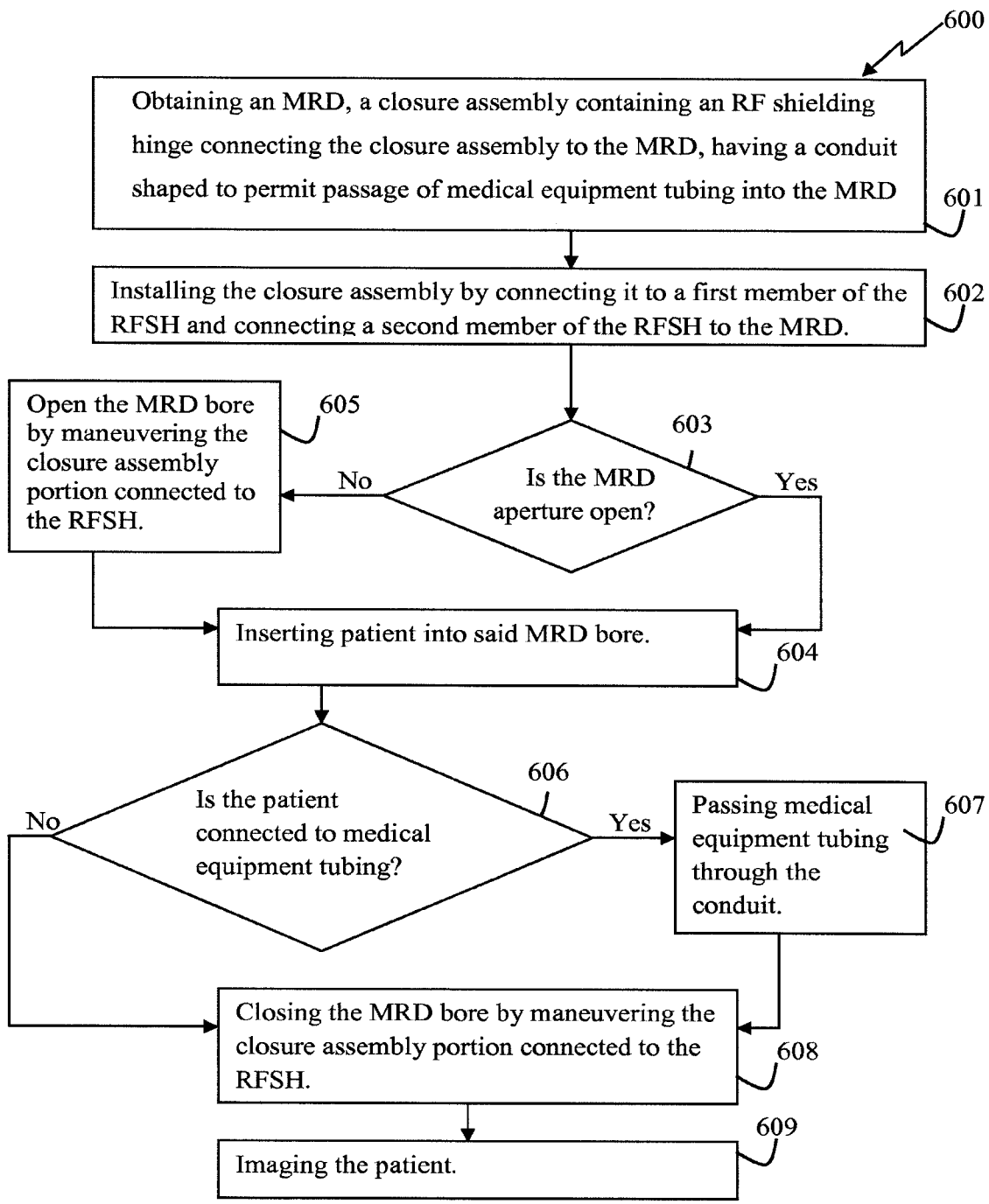
FIG. 6 is a schematic flowchart presenting a method of RF shielding an MRD from its external environment generated EMI, and RF shielding the external environment from the MRD generated EMI using an RF shielding hinge.

Reference is now made to FIG. 6 presenting a schematic flowchart (600) describing a method of RF shielding an MRD from its external environment generated EMI, and RF shielding the external environment from the MRD generated EMI using an RF shielding hinge. The first step (601) is to obtain an MRD comprising an open bore, an RF shielding hinge (RFSH) comprising at least one first connecting member and at least one second connecting member, a closure assembly designed to cover the open bore aperture. At least one first connecting member is maneuverably coupled to at least one second connecting member. Further the RFSH comprises a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding. Further this conduit is shaped to allow installation and passage of medical equipment tubing of various sizes and shapes into the MRD bore from the external environment and contrariwise. The next step (602) is installing the closure assembly to the RFSH first connecting member and the RFSH second connecting member into to the MRD. Following, if the MRD bore is open (603) insert the patient into the MRD bore (605). If closed, open the closure assembly first by maneuvering the closure assembly portion connected to the RFSH (604). If the patient is connected to medical equipment (606), the next step is to tunnel the medical equipment from the patient within the MRD bore through the RF shielding conduit to the external environment (607). Following, close the MRD bore with the closure assembly (608), while the patient is still connected to medical equipment tubing. The last step is to image the patient (609).

FIGS. 7A-7D are illustrations of a radiofrequency (RF) shielding conduit 700 to be embedded in a door 92 and/or a doorframe 91 of a magnetic resonance imaging (MRI) room 90, according to various embodiments of the invention.

Figure 7A:
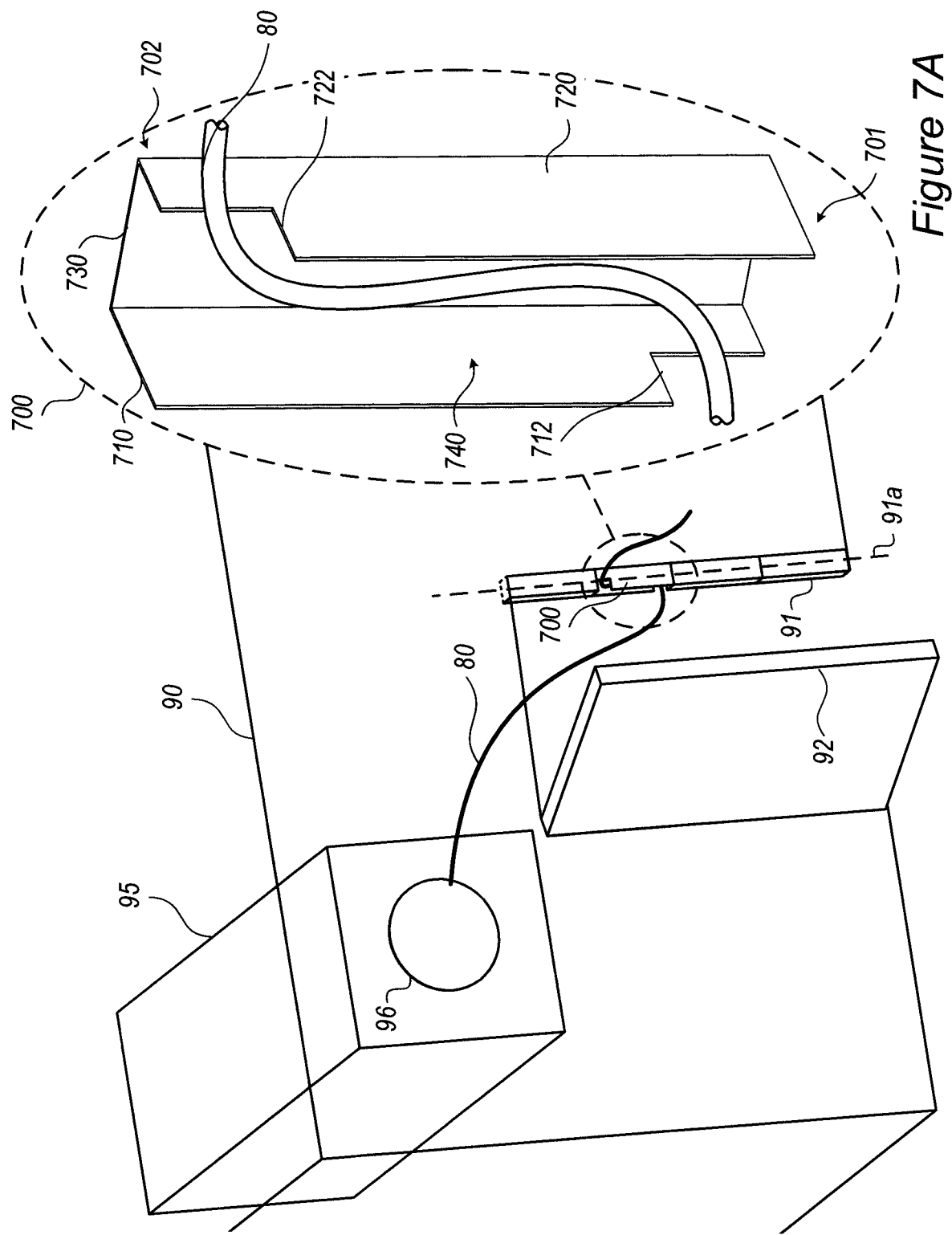
FIGS. 7A-7D are illustrations of a radiofrequency (RF) shielding conduit to be embedded in a door and/or a doorframe of a magnetic resonance imaging (MRI) room, according to various embodiments of the invention.
Figure 7B:
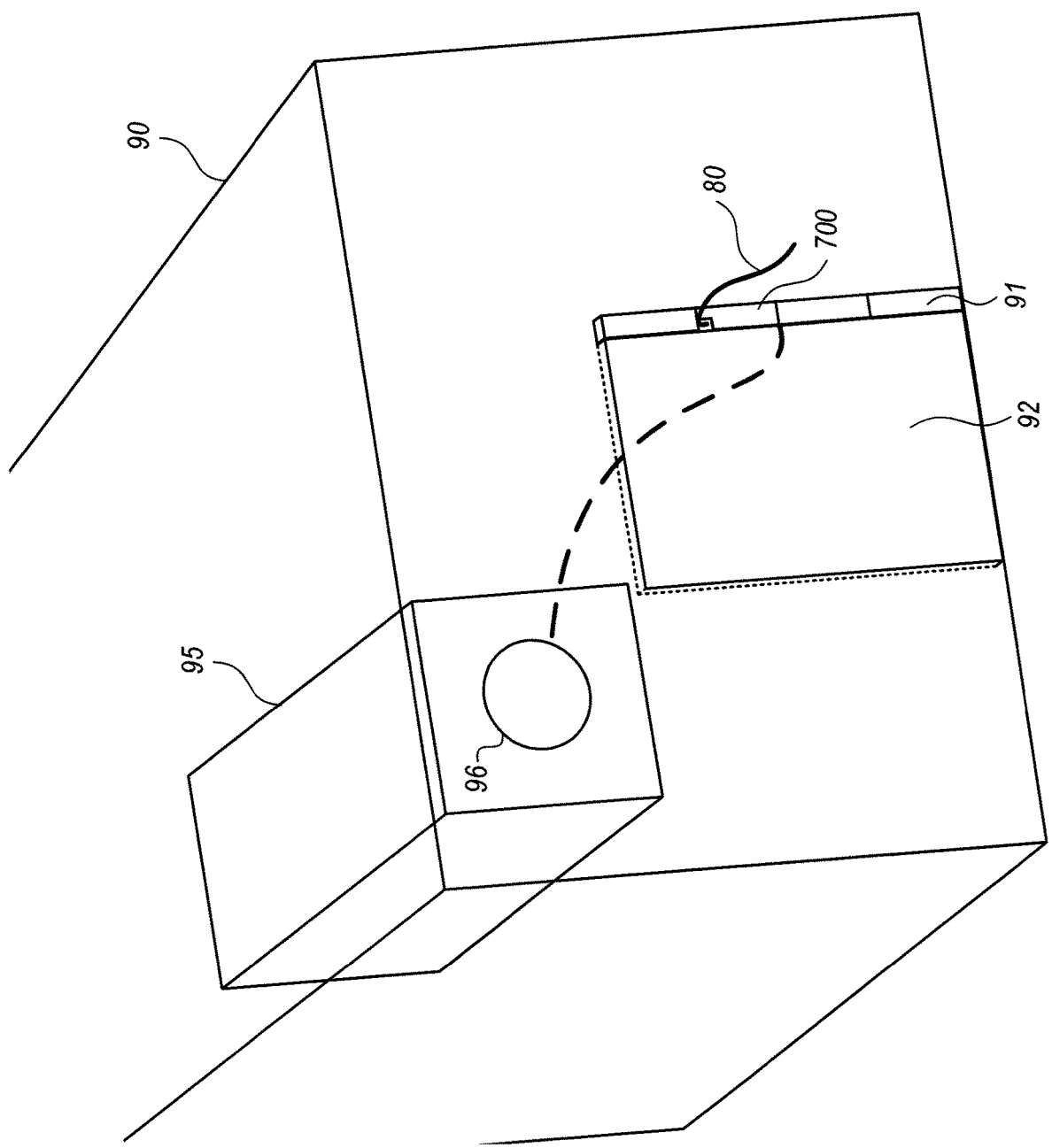

FIGS. 7A-7B present an RF shielding conduit 700 (e.g., conduit 100 as described above with respect to FIG. 2A) embedded in a doorframe 91 of the MRI room 90. FIGS. 7A, 7B present a door 92 of the MRI room 90 in open and closed states, respectively. The RF shielding conduit 700 can include a first wall 710 and a second wall 720. The first and/or second walls 710, 720, respectively, can be substantially parallel to a longitudinal axis 91a of the doorframe 91. In some embodiments, the first wall 710 is positioned closer to an interior of the MRI room 90 and/or the second wall 720 is positioned closer to an environment that is external to the MRI room 90.

The RF shielding conduit 700 can include a third wall 730 connected to the first and/or second walls 710, 720, respectively. The third wall 730 can also be substantially parallel to the longitudinal axis 91a of the doorframe 91 (e.g., as shown in FIG. 7A). In various embodiments, the first, second and/or third walls 710, 720, 730 include an electroconductive material, for example, aluminum and/or copper.

The RF shielding conduit 700 can have a first end 701 and/or a second end 702. The first and/or second walls 710, 720 can include openings (e.g., indents) 712, 722, respectively, positioned at the opposite ends 701, 702. In some embodiments, opening 712 of the first wall 710 is positioned at the first end 701 and/or opening 722 of the second wall 720 is positioned at the second end 702 of the RF shielding conduit 700 (e.g., as shown in FIG. 7A).

The RF shielding conduit 700 can include a gap 740. The gap 740 can be at least partly bounded by the first, second and/or third walls 710, 720, 730. In some embodiments, the gap 740 has a substantially U-shape cross-section in a transverse direction with respect to the longitudinal axis 91a. In various embodiments, the gap 740 has a shape selected from a group consisting of: curved U-shape, polygonal U-shape, C-shaped, V-shaped and/or any combination thereof. In some embodiments, openings 712, 722 and/or the gap 740 allow insertion of a tubing 80 of medical equipment extending from the interior of the MRI room 90 to the environment that is external to the MRI room 90 into the RF shielding conduit 700 without a need to disconnect the tubing 80 from a patient and/or from the medical equipment (e.g., as shown in FIG. 7A).

The RF shielding conduit 700 can form, upon closing of the door 92 onto the doorframe 91 of the MRI room 90, an RF shielding channel (e.g., as shown in FIG. 7B) to provide an RF shielding of the MRI room 90. The RF shielding of the MRI room 90 can include preventing an external RF radiation from entering the interior of the MRI room 90 and/or from an RF radiation emitted by the MRI device 95 from exiting the interior of the MRI room 90. In some embodiments, a ratio of a longitudinal dimension (e.g., length) to a transverse dimension (e.g., width) of the RF shieling conduit 700 and/or the RF shielding channel is at least 5:1.

In some embodiments, the RF shielding channel encloses the tubing 80 of medical equipment extending from the interior of the MRI room 90 to the environment that is external to the MRI room 90 (e.g., as shown in FIG. 7B) while providing the RF shielding of the MRI room 90. In various embodiments, the RF channel and/or at least one of the first, second and/or third walls 710, 720, 730 are grounded (e.g., connected to the ground of the system).

Figure 7C:
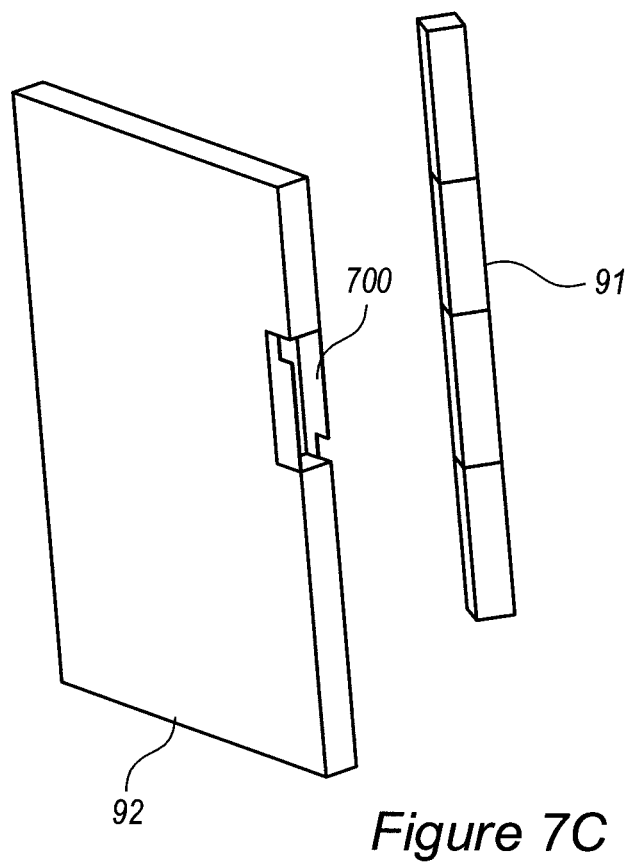
Figure 7D:
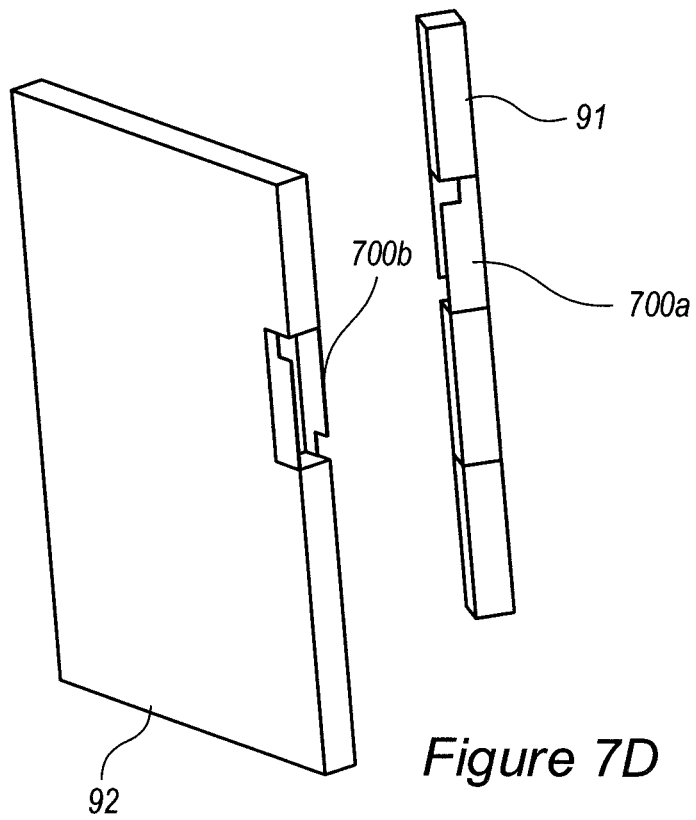

In some embodiments, the RF shielding conduit 700 is embedded within the door 92 of the MRI room 90, for example as shown in FIG. 7C. In various embodiments, more than one RF shielding conduit 700 is embedded within the doorframe 91 and/or the door 92 of the MRI room 90. For example, RF shielding conduit 700a can be embedded in the doorframe 91 and/or RF shielding conduit 700b can be embedded in the door 92 (e.g., as shown in FIG. 7D). The RF shielding conduits 700a, 700b, respectively can be positioned at a same level to provide, upon closing of the door 92 onto the doorframe 91, the RF shielding channel.

One advantage of the present invention can include providing the RF shielding of the MRI room (e.g., by the RF shielding conduit 700) while enabling the passage of the tubing of medical equipment extending from the interior of the MRI room to the environment that is external to the MRI room without a need to disconnect the tubing from the patient and/or from the medical equipment.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A closure assembly for opening and closing a bore of a magnetic resonance imaging (MRI) device, the closure assembly comprising:
   a perimeter; and
   a radio frequency (RF) shielding conduit, the RF shielding conduit comprising:
   a first aperture positioned at a first location on the RF shielding conduit and a second aperture positioned at a second location on the RF shielding conduit to accommodate passage of medical equipment tubing from an external environment of the MRI to an internal environment of the MRI, and
   an elongated opening extending along the length of the RF shielding conduit such that the medical equipment tubing can be removed from the RF shielding conduit without disconnecting the tubing from a patient and associated medical equipment,
   wherein the RF shielding conduit is located along at least a portion of the perimeter.

2. The assembly of claim 1, wherein the RF shielding conduit has a length to width ratio that attenuates electromagnetic radiation as it travels between the first aperture and the second aperture.

3. The assembly of claim 2, wherein the length to width ratio is at least 5 to 1.

4. The assembly of 10, wherein the electromagnetic radiation that is attenuated has a frequency range from 0 to 1000 megahertz.

5. The assembly of claim 1, wherein the RF shielding conduit comprises at least three walls, and wherein at least one of the apertures is positioned in one of the at least three walls.

6. The assembly of claim 1, wherein:
the RF shielding conduit comprises three walls,
each of the three walls has a first end and a second end,
each of the first ends of the three walls is opposite each of the second ends of the three walls,
each of the first ends of the three walls defines a first opening, and
one of the apertures is the first opening.

7. The assembly of claim 6, wherein the first opening is planar.

8. The assembly of claim 1, wherein the RF shielding conduit comprises three walls, wherein one wall is shorter in length than the other two walls, thereby forming a second opening in the RF shielding conduit, and wherein one of the apertures is the second opening.

9. The assembly of claim 8, wherein the second opening is disposed in the one wall that is shorter in length than the other walls.

\* \* \* \* \*